US006451300B1

United States Patent
Dunlop et al.

(10) Patent No.: US 6,451,300 B1
(45) Date of Patent: *Sep. 17, 2002

(54) ANTI-DANDRUFF AND CONDITIONING SHAMPOOS CONTAINING POLYALKYLENE GLYCOLS AND CATIONIC POLYMERS

(75) Inventors: David Scott Dunlop, Mason; Susan Marie Guskey, Montgomery, both of OH (US); Vicente Eduardo Leyba, Los Ruices (VE); Douglas Allan Royce, Aurora, IN (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/558,447

(22) Filed: Apr. 25, 2000

Related U.S. Application Data

(60) Provisional application No. 60/132,869, filed on May 3, 1999.

(51) Int. Cl.$^7$ .................. A61K 7/06; A61K 7/075
(52) U.S. Cl. ............ 424/70.27; 424/70.1; 424/70.8; 424/70.22; 424/70.11; 424/70.12; 424/70.13
(58) Field of Search ............... 424/70.1, 70.8, 424/70.22, 70.11, 70.12, 70.13

(56) References Cited

U.S. PATENT DOCUMENTS

| | | | |
|---|---|---|---|
| 3,580,853 A | 5/1971 | Parran | 252/152 |
| 4,557,928 A | 12/1985 | Glover | 424/70 |
| 5,037,818 A | 8/1991 | Sime | 514/183 |
| 5,085,857 A | 2/1992 | Reid et al. | 424/70 |
| 5,104,645 A | 4/1992 | Cardin et al. | 424/70 |
| RE34,584 E | 4/1994 | Grote et al. | 252/142 |
| 5,543,074 A | 8/1996 | Hague et al. | 510/122 |
| 5,624,666 A | 4/1997 | Coffindaffer et al. | 424/70 |
| 5,723,112 A | 3/1998 | Bowser et al. | 424/70 |
| 5,747,435 A | 5/1998 | Patel | 510/119 |
| 5,756,436 A | 5/1998 | Royce et al. | 510/122 |
| 5,776,871 A | 7/1998 | Cothran et al. | 150/122 |
| 5,837,661 A | 11/1998 | Evans et al. | 510/122 |
| 5,854,266 A | 12/1998 | Nelson, Jr. | 514/345 |
| 5,876,705 A | 3/1999 | Uchiyama et al. | 424/70 |
| 5,935,561 A | 8/1999 | Inman et al. | 424/70.19 |
| 5,977,036 A | 11/1999 | Guskey | 510/121 |
| 5,977,038 A | 11/1999 | Birtwistle et al. | 510/122 |
| 6,010,990 A | 1/2000 | Rousso et al. | 510/124 |

FOREIGN PATENT DOCUMENTS

| | | | |
|---|---|---|---|
| EP | 007704 | 6/1979 | A61K/7/06 |
| EP | 060611 | 1/1982 | A61K/7/06 |
| EP | 093541 | 4/1983 | A61K/7/06 |
| EP | 117135 | 2/1984 | C11D/3/37 |
| EP | 173259 | 8/1985 | A61K/7/06 |
| EP | 497163 | 8/1992 | A61K/7/06 |
| EP | 530974 | 8/1992 | A61K/7/06 |
| EP | 432951 | 10/1993 | A61K/7/075 |
| EP | 800814 | 10/1997 | A61K/7/06 |
| JP | 58-029900 | 2/1983 | A61K/7/06 |
| JP | 05-310540 | 11/1992 | A61K/7/075 |
| JP | 10-175827 | 6/1998 | A61K/7/075 |
| WO | WO 93/08787 | 5/1993 | A61K/7/06 |
| WO | WO 95/09599 | 4/1995 | A61K/7/06 |
| WO | 96/29983 | 10/1996 | A61K/7/50 |
| WO | WO 97/26854 | 7/1997 | A61K/7/06 |
| WO | 97/35542 | 10/1997 | A61K/7/06 |
| WO | WO 98/16189 | 4/1998 | A61K/7/06 |
| WO | WO 98/18434 | 5/1998 | A61K/7/06 |
| WO | WO 98/52927 | 11/1998 | C07D/241/36 |
| WO | WO 99/26585 | 6/1999 | A61K/7/00 |
| WO | 99/39683 | 8/1999 | A61K/7/06 |
| WO | 99/66886 | 12/1999 | A61K/7/06 |

Primary Examiner—Thurman K. Page
Assistant Examiner—S. Howard
(74) Attorney, Agent, or Firm—Brent M. Peebles; Andrew A. Paul; Tara M. Rosnell

(57) ABSTRACT

Disclosed are shampoo compositions that provide a superior combination of anti-dandruff efficacy and conditioning, and a method of cleansing and conditioning the hair comprising applying to the hair and scalp an effective amount of said compositions. The anti-dandruff and conditioning shampoos comprise: (A) from about 5% to about 50%, by weight of the composition, of an anionic surfactant; (B) from about 0.01% to about 10%, by weight of the composition, of a non-volatile conditioning agent; (C) from about 0.1% to about 4%, by weight of the composition, of an anti-dandruff particulate; (D) from about 0.02% to about 5%, by weight of the composition, of at least one cationic polymer; (E) from 0.005% to about 1.5%, by weight of the composition, of a polyalkylene glycol corresponding to the formula: $H(OCH_2—CHR)_n—OH$, (i) wherein R is selected from the group consisting of hydrogen, methyl and mixtures thereof, (ii) wherein n is an integer having an average value from about 1,500 to about 120,000; and (F) water.

25 Claims, No Drawings

ANTI-DANDRUFF AND CONDITIONING SHAMPOOS CONTAINING POLYALKYLENE GLYCOLS AND CATIONIC POLYMERS

This application claims priority of Provisional application Ser. No. 60/132,869 filed May 3, 1999.

TECHNICAL FIELD OF THE INVENTION

The present invention relates to shampoo compositions which provide a superior combination of anti-dandruff efficacy and conditioning. These compositions contain anionic surfactants, conditioning agents, anti-dandruff particulates, cationic polymers, polyalkylene glycols, and water.

BACKGROUND OF THE INVENTION

Shampoo compositions comprising various combinations of detersive surfactants and conditioning agents, especially silicone conditioning agents, are known in the art and are commercially available. Many of these compositions have been found to provide excellent hair cleansing and conditioning performance. For example, Pantene® Shampoo Plus Pro-Vitamin Conditioner-in-One formulas which contain anionic surfactants, a cationic polymer and silicone conditioning agents provide excellent cleaning, conditioning and hair feel benefits upon application to hair.

Anti-dandruff shampoos are also well known in the art and are also commercially available. Anti-dandruff shampoos typically incorporate an anti-dandruff active and detersive surfactants. Among the preferred type of anti-dandruff agents are particulate, crystalline anti-dandruff agents, such as sulfur, selenium disulfide and heavy metal salts of pyridinethione. Soluble anti-dandruff agents, such as ketoconazole, are also known in the art.

Anti-dandruff shampoos which also provide conditioning benefits are likewise known in the art. For example, U.S. Pat. No. 5,624,666 exemplifies and claims shampoo compositions which contain anionic surfactants, cationic polymers and zinc pyridinethione as an anti-dandruff agent. U.S. Pat. No. 5,624,666 teaches that conditioning agents such as silicone fluids can optionally be incorporated into the compositions therein. Head & Shoulders® Dandruff Shampoo Plus Conditioner is an example of a marketed product which provides both anti-dandruff and conditioning benefits upon application of the shampoo to hair.

Nevertheless, some consumers desire a shampoo which provides a superior combination of anti-dandruff efficacy and conditioning performance versus currently marketed products. Such a superior combination of efficacy and conditioning can be difficult to achieve.

For example, it was previously believed that excellent anti-dandruff efficacy could be achieved by utilizing a coacervate to deposit anti-dandruff actives on the hair and scalp. Unfortunately, the use of coacervates to deposit anti-dandruff actives on the hair or scalp can negatively affect conditioning, specifically clean hair feel. In order to achieve good conditioning, the level of anti-dandruff agent could be reduced, resulting in good conditioning, but less than optimal anti-dandruff efficacy.

Applicants have now discovered, however, that, surprisingly, bioavailability and coverage of the anti-dandruff active are much more predictive of efficacy than deposition of the active on the hair or scalp. In fact, Applicants have found that, in some cases, even when an anti-dandruff active deposited very well on the hair and scalp, acceptable anti-dandruff efficacy was not achieved. Conversely, good anti-dandruff efficacy could be achieved in situations where the anti-dandruff active had good coverage and was highly bioavailable, but did not deposit superiorly to the hair or scalp. Thus, in order for a shampoo composition to provide a superior combination of anti-dandruff efficacy and conditioning compared to known shampoo compositions, it must meet certain criteria with respect to bioavailability and coverage, but it does not necessarily have to have the ability to deposit the anti-dandruff active superiorly on the hair or scalp.

It is an object of the present invention to provide shampoo compositions, which provide a superior combination of anti-dandruff efficacy and conditioning. It is also an object of the present invention to provide a method for cleansing and conditioning the hair. These, and other objects, will become readily apparent from the detailed description below.

SUMMARY OF THE INVENTION

The present invention relates to shampoo compositions which provide a superior combination of anti-dandruff efficacy and conditioning. These shampoo compositions comprise: (A) from about 5% to about 50%, by weight, of an anionic surfactant; (B) from about 0.01% to about 10%, by weight, of a non-volatile conditioning agent; (C) from about 0.1% to about 4%, by weight, of an anti-dandruff particulate; (D) from about 0.02% to about 5%, by weight of the composition, of at least one cationic polymer; (E) from 0.005% to about 1.5%, by weight, of a polyalkylene glycol; and (F) water. The polyalkylene glycol corresponds to the formula $H(O-CH_2-CHR)_n-OH$, wherein R is hydrogen, methyl or mixtures thereof, and n is an integer having an average value from about 1,500 to about 120,000.

The present invention further relates to a method for providing anti-dandruff efficacy and conditioning hair comprising applying to the hair and scalp an amount of the above-described composition which is effective to provide such benefits.

DETAILED DESCRIPTION OF THE INVENTION

The shampoo compositions of the present invention provide a superior combination of anti-dandruff efficacy and conditioning. Such anti-dandruff and conditioning shampoo compositions of the present invention can comprise, consist of, or consist essentially of the essential elements and limitations of the invention described herein, as well as any of the additional or optional ingredients, components or limitations described herein.

Particularly, these compositions comprise anionic surfactants, conditioning agents, anti-dandruff particulates, cationic polymers, polyalkylene glycols and water. Upon dilution, the anionic surfactants and cationic polymers form a coacervate, and the type and level of polyalkylene glycol employed will influence the amount of anti-dandruff particulates that are bioavailable. This is important for anti-dandruff efficacy and conditioning.

The components, including those which may optionally be added, of the shampoo compositions of the present invention, as well as methods for preparation, and methods for use, are described in detail below.

I. Components

The anti-dandruff and conditioning shampoo compositions of the present invention comprise an anionic surfactant, a conditioning agent, an anti-dandruff particulate, at least one cationic polymer, a polyalkylene glycol, and water. Each of these ingredients is described in detail below.

A. Anionic Surfactant

The anti-dandruff and conditioning shampoo compositions of the present invention comprise from about 5% to about 50%, by weight of the composition, preferably from about 8% to about 30%, more preferably from about 10% to about 25%, most preferably from about 12% to about 18%, of an anionic detersive surfactant component suitable for application to the hair or skin. The anionic detersive surfactant is believed to provide cleaning and lather performance to the composition. Additionally, the anionic detersive surfactant forms a coacervate, upon aqueous dilution, with the cationic polymer component (described below) of the present invention. This coacervate is believed to be important in providing the efficacy and conditioning benefits described herein.

The anionic detersive surfactant component can comprise an anionic detersive surfactant, a zwitterionic or an amphoteric detersive surfactant having an attached moiety that is anionic at the pH of the composition, or a combination thereof, preferably an anionic detersive surfactant. Such surfactants should be physically and chemically compatible with the essential components described herein, and should not otherwise unduly impair product stability, aesthetics or performance. Examples of anionic detersive surfactants which may be suitably employed in the shampoo compositions herein include, but are not limited to: sulfates, sulfonates, sarcosinates and sarcosine derivatives.

1. Sulfates

Preferred anionic detersive surfactants for use in the anti-dandruff and conditioning shampoo compositions of the present invention are the alkyl and alkyl ether sulfates. These surfactants have the respective formulae $ROSO_3M$ and $R(C_2H_4O)_xOSO_3M$, wherein R is alkyl or alkenyl from about $C_8$ to about $C_{18}$, x is an integer having a value from 1 to 10, and M is a cation selected from the group consisting of electropositive covalently bonded moieties (e.g. ammonium), alkanolamines (e.g. triethanolamine), monovalent metals (e.g. sodium or potassium), polyvalent metal cations (e.g. magnesium and calcium) and mixtures thereof. The cation M should be selected such that the anionic detersive surfactant component is water soluble. Solubility of the surfactant will depend upon the particular anionic detersive surfactants and cations chosen.

Preferably, R is from about $C_8$ to about $C_{18}$, more preferably from about $C_{10}$ to about $C_{16}$, most preferably from about $C_{12}$ to about $C_{14}$, in both the alkyl and alkyl ether sulfates. The alkyl ether sulfates are typically made as condensation products of ethylene oxide and monohydric alcohols from about $C_8$ to about $C_{24}$. The alcohols can be synthetic or they can be derived from fats, e.g., coconut oil, palm kernel oil, and tallow. Lauryl alcohol and straight chain alcohols derived from coconut oil or palm kernel oil are preferred. Such alcohols are reacted with from 0 to about 10, preferably from about 2 to about 5, most preferably about 3, moles of ethylene oxide. The resulting mixture of molecular species will have, for example, an average of 3 moles of ethylene oxide per mole of alcohol, and is sulfated and neutralized.

Non-limiting examples of alkyl ether sulfates which may be used in the shampoo compositions of the present invention include sodium and ammonium salts of coconut alkyl triethylene glycol ether sulfate, tallow alkyl triethylene glycol ether sulfate, and tallow alkyl hexa-oxyethylene sulfate. Preferred alkyl ether sulfates are those comprising a mixture of individual compounds, wherein the compounds in the mixture have an average alkyl chain length from about $C_{10}$ to about $C_{16}$ and an average degree of ethoxylation of from about 1 to about 4 moles of ethylene oxide.

Specific examples of preferred alkyl sulfates include, but are not limited to, ammonium lauryl sulfate, ammonium cocoyl sulfate, potassium lauryl sulfate, potassium cocoyl sulfate, sodium lauryl sulfate, sodium cocoyl sulfate, monoethanolamine lauryl sulfate, monoethanolamine cocoyl sulfate, diethanolamine lauryl sulfate, triethanolamine lauryl sulfate, triethylamine lauryl sulfate, and mixtures thereof. Especially preferred is ammonium lauryl sulfate.

Specific examples of preferred alkyl ether sulfates include, but are not limited to, ammonium laureth sulfate, potassium laureth sulfate, sodium laureth sulfate, monoethanolamine laureth sulfate, diethanolamine laureth sulfate, triethanolamine laureth sulfate, triethylamine laureth sulfate, and mixtures thereof. Especially preferred is ammonium laureth sulfate.

Still another class of sulfate surfactants suitable for use in the for use in the anti-dandruff and conditioning shampoos of the present invention are the sulfated glycerides, an example of which includes, but is not limited to, lauric monoglyceride sodium sulfate.

2. Sulfonates

Also suitable for use in the anti-dandruff and conditioning shampoos of the present invention are those anionic detersive surfactants known as olefin sulfonates. As used herein, the term "olefin sulfonates" refers to compounds which can be produced by the sulfonation of α-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydro-carbons, and the like, when used in the liquid form, or by air, nitrogen, gaseous $SO_2$, and the like, when used in the gaseous form. The α-olefins from which the olefin sulfonates are derived are mono-olefins which are from about $C_{10}$ to about $C_{24}$, preferably from about $C_{12}$ to about $C_{16}$. Preferably, they are straight chain olefins. In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A non-limiting example of such an α-olefin sulfonate mixture is described in U.S. Pat. No. 3,332,880, which description is incorporated herein by reference.

Another class of sulfonates suitable for use in the anti-dandruff and conditioning shampoo compositions of the present invention are those anionic detersive surfactants known as β-alkyloxy alkane sulfonates. These surfactants conform to the general Formula (I):

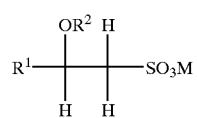

where $R^1$ is a straight chain alkyl group from about $C_6$ to about $C_{20}$, $R^2$ is a lower alkyl group from about $C_1$ to about $C_3$, preferably $C_1$, and M is a water-soluble cation, as described above.

Still other sulfonates suitable for use in the anti-dandruff and conditioning shampoo compositions of the present invention are those anionic detersive surfactants known as alkyl aryl sulfonates. Non-limiting examples of alkyl aryl sulfonates include sodium tridecyl benzene sulfonate, sodium dodecyl benzene sulfonate, and mixtures thereof.

Other suitable sulfonates for use in the anti-dandruff and conditioning shampoos of the present invention are the water-soluble salts of organic, sulfuric acid reaction products conforming to the formula [$R^1$—$SO_3$—M] where $R^1$ is a straight or branched chain, saturated, aliphatic hydrocarbon radical from about $C_8$ to about $C_{24}$, preferably about $C_{10}$ to about $C_{18}$; and M is a cation described above. Non-limiting examples of such anionic detersive surfactants are the salts of an organic sulfuric acid reaction product of a hydrocarbon of the methane series, including iso-, neo-, and n-paraffins, and a sulfonating agent, e.g., $SO_3$, $H_2SO_4$, obtained according to known sulfonation methods. The sulfonation methods may include bleaching and hydrolysis. The salts are preferably from about $C_8$ to about $C_{24}$; more preferably from about $C_{12}$ to about $C_{18}$. Preferred are alkali metal and ammonium sulfonated $C_{10}$ to $C_{18}$ n-paraffins.

Still other suitable sulfonates for use in the anti-dandruff and conditioning shampoo compositions of the present invention are the reaction products of fatty acids, which are esterified with isethionic acid, and then neutralized with sodium hydroxide. Preferred fatty acids are those derived from coconut oil or palm kernel oil. Also suitable are the sodium or potassium salts of fatty acid amides of methyl tauride in which the fatty acids are derived from coconut oil or palm kernel oil. Other similar anionic surfactants are described in U.S. Pat. Nos. 2,486,921: 2,486,922; and 2,396,278, which descriptions are incorporated herein by reference.

Other sulfonates suitable for use in the anti-dandruff and conditioning shampoo compositions of the present invention are the succinnates, examples of which include, but are not limited to, disodium N-octadecylsulfosuccinate, disodium lauryl sulfosuccinate, diammonium lauryl sulfosuccinate, tetrasodium N-(1,2-dicarboxyethyl)-N-octadecylsulfosuccinnate, diamyl ester of sodium sulfosuccinic acid, dihexyl ester of sodium sulfosuccinic acid, dioctyl esters of sodium sulfosuccinic acid, and mixtures thereof.

3. Sarcosinates and Sarcosine Derivatives

Also suitable for use in the anti-dandruff and conditioning shampoos of the present invention are those anionic detersive surfactants known as sarcosinates and sarcosine derivatives. Sarcosinates are the derivatives of sarcosine and N-methyl glycine, acylated with a fatty acid chloride. They conform to the general Formula (II):

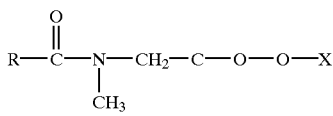

wherein RCO— is a fatty acid radical and wherein X is either hydrogen (acid form) or a cationic species, such as Na$^+$ or TEA$^+$ (salt form). Non-limiting examples of sarcosinates and sarcosine derivatives include: sodium lauryl sarcosinate, lauryl sarcosine, cocoyl sarcosine, and mixtures thereof. A preferred sarcosinate is sodium lauryl sarcosinate.

B. Conditioning Agent

The anti-dandruff and conditioning shampoo compositions of the present invention comprise from about 0.01% to about 10%, by weight of the composition, preferably from about 0.1% to about 8%, more preferably from about 0.1% to about 5%, most preferably from about 0.2% to about 3.5%, of a conditioning agent suitable for application to the hair or skin. It is believed that the conditioning agent provides improved conditioning benefits to the hair, particularly clean hair feel and wet rinse feel.

The conditioning agent comprises a water insoluble, water dispersible, non-volatile, liquid that forms emulsified, liquid particles or are solubilized by the surfactant micelles, in the anionic detersive surfactant component (described above). Suitable conditioning agents for use in the shampoo composition are those conditioning agents characterized generally as silicones (e.g. silicone oils, cationic silicones, silicone gums, high refractive silicones, and silicone resins), organic conditioning oils (e.g. hydrocarbon oils, polyolefins, and fatty esters) or combinations thereof, or those conditioning agents which otherwise form liquid, dispersed, particles in the aqueous surfactant matrix herein. Such conditioning agents should be physically and chemically compatible with the essential components of the composition, and should not otherwise unduly impair product stability, aesthetics or performance.

The concentration of the conditioning agent in the shampoo composition should be sufficient to provide the desired conditioning benefits, and as will be apparent to one of ordinary skill in the art. Such concentration can vary with the conditioning agent, the conditioning performance desired, the average size of the conditioning agent particles, the type and concentration of other components, and other like factors.

1. Silicones

The conditioning agent of the anti-dandruff and conditioning shampoo compositions of the present invention is preferably an insoluble silicone conditioning agent. The silicone conditioning agent particles may comprise volatile silicone, non-volatile silicone, or combinations thereof. Preferred are non-volatile silicone conditioning agents. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair (especially when high refractive index (e.g. above about 1.46) silicone conditioning agents are used (e.g. highly phenylated silicones).

The concentration of the silicone conditioning agent typically ranges from about 0.01% to about 10%, by weight of the composition, preferably from about 0.1% to about 8%, more preferably from about 0.1% to about 5%, most preferably from about 0.2% to about 3%. Non-limiting examples of suitable silicone conditioning agents, and optional suspending agents for the silicone, are described in U.S. Reissue Pat. No. 34,584, U.S. Pat. Nos. 5,104,646, and 5,106,609, which descriptions are incorporated herein by reference. The silicone conditioning agents for use in the anti-dandruff and conditioning shampoo compositions of the present invention preferably have a viscosity, as measured at 25° C., from about 20 to about 2,000,000 centistokes ("csk"), more preferably from about 1,000 to about 1,800,000 csk, even more preferably from about 50,000 to about 1,500,000 csk, most preferably from about 100,000 to about 1,500,000 csk.

The dispersed, silicone conditioning agent particles typically have a number average particle diameter ranging from about 0.0.1 μm to about 50 μm. For small particle application to hair, the number average particle diameters typically range from about 0.01 μm to about 4 μm, preferably from about 0.01 μm to about 2 μm, more preferably from about 0.01 μm to about 0.5 μm. For larger particle application to hair, the number average particle diameters typically range from about 4 μm to about 50 μm, preferably from about 6 μm to about 30 μm, more preferably from about 9 μm to about 20 μm, most preferably from about 12 μm to about 18 μm. Conditioning agents having an average particle size of less than about 5 μm may deposit more efficiently on the hair. It is believed that small size particles of conditioning agent are contained within the coacervate that is formed between the anionic surfactant component (described above) and the cationic polymer component (described below), upon dilution of the shampoo.

Background material on silicones including sections discussing silicone fluids, gums, and resins, as well as manufacture of silicones, are found in *Encyclopedia of Polymer Science and Engineering*, vol. 15, 2d ed., pp 204–308, John Wiley & Sons, Inc. (1989), incorporated herein by reference.

i. Silicone Oils

Silicone fluids include silicone oils, which are flowable silicone materials having a viscosity, as measured at 25° C., less than 1,000,000 csk, preferably from about 5 csk to about 1,000,000 csk, more preferably from about 10 csk to about 100,000 csk. Suitable silicone oils for use in the anti-dandruff and conditioning shampoo compositions of the present invention include polyalkyl siloxanes, polyaryl siloxanes, polyalkylaryl siloxanes, polyether siloxane copolymers, and mixtures thereof. Other insoluble, non-volatile silicone fluids having hair conditioning properties may also be used.

Silicone oils include polyalkyl or polyaryl siloxanes which conform to the following Formula (III):

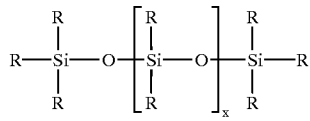

wherein R is aliphatic, preferably alkyl or alkenyl, or aryl, R can be substituted or unsubstituted, and x is an integer from 1 to about 8,000. Suitable unsubstituted R groups for use in the anti-dandruff and conditioning shampoo compositions of the present invention include, but are not limited to: alkoxy, aryloxy, alkaryl, arylalkyl, arylalkenyl, alkamino, and ether-substituted, hydroxyl-substituted, and halogen-substituted aliphatic and aryl groups. Suitable R groups also include cationic amines and quaternary ammonium groups.

The aliphatic or aryl groups substituted on the siloxane chain may have any structure so long as the resulting silicones remain fluid at room temperature, are hydrophobic, are neither irritating, toxic nor otherwise harmful when applied to the hair, are compatible with the other components of the shampoo compositions, are chemically stable under normal use and storage conditions, are insoluble in the shampoo compositions herein, and are capable of being deposited on and conditioning the hair. The two R groups on the silicon atom of each monomeric silicone unit may represent the same or different groups. Preferably, the two R groups represent the same group.

Preferred alkyl and alkenyl substituents are $C_1$ to $C_5$ alkyls and alkenyls, more preferably from $C_1$ to $C_4$, most preferably from $C_1$ to $C_2$. The aliphatic portions of other alkyl-, alkenyl-, or alkynyl-containing groups (such as alkoxy, alkaryl, and alkamino) can be straight or branched chains, and are preferably from $C_1$ to $C_5$, more preferably from $C_1$ to $C_4$, even more preferably from $C_1$ to $C_3$, most preferably from $C_1$ to $C_2$. As discussed above, the R substituents can also contain amino functionalities (e.g. alkamino groups), which can be primary, secondary or tertiary amines or quaternary ammonium. These include mono-, di- and tri-alkylamino and alkoxyamino groups, wherein the aliphatic portion chain length is preferably as described above. The R substituents may also be substituted with other groups, such as halogens (e.g. chloride, fluoride, and bromide), halogenated aliphatic or aryl groups, hydroxy (e.g. hydroxy substituted aliphatic groups), and mixtures thereof. Suitable halogenated R groups could include, for example, tri-halogenated (preferably tri-fluoro) alkyl groups such as —$R^1CF_3$, wherein $R^1$ is a $C_1$–$C_3$ alkyl. An example of such a polysiloxane includes, but is not limited to, polymethyl 3,3,3-trifluoropropylsiloxane.

Suitable R groups for use in the anti-dandruff and conditioning shampoo compositions of the present invention include, but are not limited to: methyl, ethyl, propyl, phenyl, methylphenyl and phenylmethyl. Specific non-limiting examples of preferred silicones include: polydimethyl siloxane, polydiethylsiloxane, and polymethylphenylsiloxane. Polydimethylsiloxane is especially preferred. Other suitable R groups include: methyl, methoxy, ethoxy, propoxy, and aryloxy. The three R groups on the end caps of the silicone may represent the same or different groups.

Non-volatile polyalkylsiloxane fluids that may be used include, for example, low molecular weight polydimethylsiloxanes. These siloxanes are available, for example, from the General Electric Company in their Viscasil R and SF 96 series, and from Dow Corning in their Dow Corning 200 series. Polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid. Polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. The ethylene oxide and polypropylene oxide concentrations must be sufficiently low to prevent solubility in water and the composition described herein.

Alkylamino substituted silicones suitable for use in the anti-dandruff and conditioning shampoo compositions of the present invention include, but are not limited to, those which conform to the following general Formula (IV):

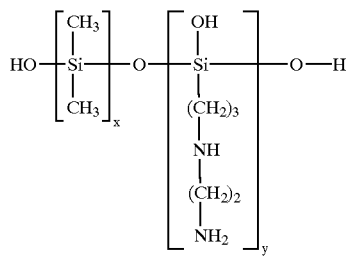

wherein x and y are integers. This polymer is also known as "amodimethicone."

ii. Cationic Silicones

Cationic silicone fluids suitable for use in the anti-dandruff and conditioning shampoo compositions of the present invention include, but are not limited to, those which conform to the general formula (V):

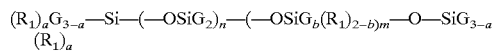

wherein G is hydrogen, phenyl, hydroxy, or $C_1$–$C_8$ alkyl, preferably methyl; a is 0 or an integer having a value from 1 to 3, preferably 0; b is 0 or 1, preferably 1; n is a number from 0 to 1,999, preferably from 49 to 149; m is an integer from 1 to 2,000, preferably from 1 to 10; the sum of n and m is a number from 1 to 2,000, preferably from 50 to 150; $R_1$ is a monovalent radical conforming to the general formula $CqH_{2q}L$, wherein q is an integer having a value from 2 to 8 and L is selected from the following groups:

—N($R_2$)$CH_2$—$CH_2$—N($R_2$)$_2$

—N($R_2$)$_2$

—N($R_2$)$_3$A$^-$

—N($R_2$)$CH_2$—$CH_2$—N$R_2H_2$A$^-$ wherein $R_2$ is hydrogen, phenyl, benzyl, or a saturated hydrocarbon radical, preferably an alkyl radical from about $C_1$ to about $C_{20}$, and A$^-$ is a halide ion.

An especially preferred cationic silicone corresponding to formula (V) is the polymer known as "trimethylsilylamodimethicone", which is shown below in formula (VI):

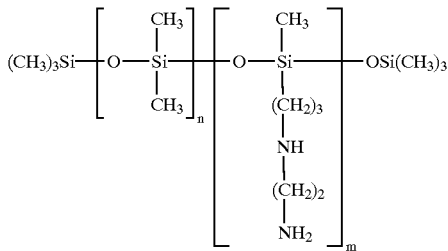

Other silicone cationic polymers which may be used in the anti-dandruff and conditioning shampoo compositions of the present invention are represented by the general formula (VII):

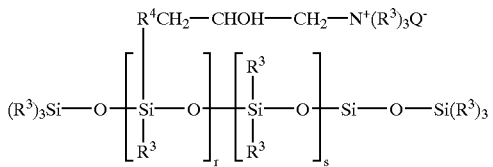

wherein $R^3$ is a monovalent hydrocarbon radical from $C_1$ to $C_{18}$, preferably an alkyl or alkenyl radical, such as methyl; $R_4$ is a hydrocarbon radical, preferably a $C_1$ to $C_{18}$ alkylene radical or a $C_{10}$ to $C_{18}$ alkyleneoxy radical, more preferably a $C_1$ to $C_8$ alkyleneoxy radical; Q$^-$ is a halide ion, preferably chloride; r is an average statistical value from 2 to 20, preferably from 2 to 8; s is an average statistical value from 20 to 200, preferably from 20 to 50. A preferred polymer of this class is known as UCARE SILICONE ALE 56™, available from Union Carbide.

iii. Silicone Gums

Other silicone fluids suitable for use in the anti-dandruff and conditioning shampoo compositions of the present invention are the insoluble silicone gums. These gums are polyorganosiloxane materials having a viscosity, as measured at 25° C., of greater than or equal to 1,000,000 csk. Silicone gums are described in U.S. Pat. No. 4,152,416; Noll and Walter, *Chemistry and Technology of Silicones,* New York: Academic Press (1968); and in General Electric Silicone Rubber Product Data Sheets SE 30, SE 33, SE 54 and SE 76, all of which are incorporated herein by reference. The silicone gums will typically have a weight average molecular weight in excess of about 200,000, preferably from about 200,000 to about 1,000,000. Specific non-limiting examples of silicone gums for use in the anti-dandruff and conditioning shampoo compositions of the present invention include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

iv. High Refractive Index Silicones

Other non-volatile, insoluble silicone fluid conditioning agents that are suitable for use in the anti-dandruff and conditioning shampoo compositions of the present invention are those known as "high refractive index silicones," having a refractive index of at least about 1.46, preferably at 25 least about 1.48, more preferably at least about 1.52, most preferably at least about 1.55. The refractive index of the polysiloxane fluid will generally be less than about 1.70, typically less than about 1.60. In this context, polysiloxane "fluid" includes oils as well as gums.

The high refractive index polysiloxane fluid includes those represented by general Formula (III) above, as well as cyclic polysiloxanes such as those represented by Formula (VIII) below:

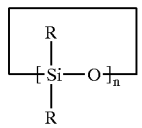

wherein R is as defined above, and n is a number from about 3 to about 7, preferably from about 3 to about 5.

The high refractive index polysiloxane fluids contain an amount of aryl-containing R substituents sufficient to increase the refractive index to the desired level, which is described above. Additionally, R and n must be selected so that the material is non-volatile.

Aryl-containing substituents include those which contain alicyclic and heterocyclic five and six member aryl rings and those which contain fused five or six member rings. The aryl rings themselves can be substituted or unsubstituted. Substituents include aliphatic substituents, and may also include alkoxy substituents, acyl substituents, ketones, halogens (e.g., Cl and Br), amines, and the like. Examples of aryl-containing groups include, but are not limited to, substituted and unsubstituted arenes, such as phenyl, and phenyl derivatives, such as phenyls with $C_1$–$C_5$ alkyl or alkenyl substituents. Specific non-limiting examples include: allylphenyl, methyl phenyl and ethyl phenyl, vinyl phenyls (e.g. styrenyl), and phenyl alkynes (e.g. phenyl $C_2$–$C_4$ alkynes). Heterocyclic aryl groups include, but are not limited to, substituents derived from furan, imidazole, pyrrole, pyridine, and the like. Examples of fused aryl ring substituents include, but are not limited to, napthalene, coumarin, and purine.

Generally, the high refractive index polysiloxane fluids will have a degree of aryl-containing substituents of at least about 15%, preferably at least about 20%, more preferably at least about 25%, even more preferably at least about 35%, most preferably at least about 50%. Typically, the degree of aryl substitution will be less than about 90%, more generally less than about 85%, preferably from about 55% to about 80%.

The high refractive index polysiloxane fluids are also characterized by relatively high surface tensions as a result of their aryl substitution. Generally, the polysiloxane fluids will have a surface tension of at least about 24 dynes/cm$^2$, typically at least about 27 dynes/cm$^2$. Surface tension, for purposes hereof, is measured by a de Nouy ring tensiometer according to Dow Corning corporate Test Method CTM 0461 (Nov. 23, 1971). Changes in surface tension can be measured according to the above test method or according to ASTM Method D 1331.

Preferred high refractive index polysiloxane fluids have a combination of phenyl or phenyl derivative substituents (most preferably phenyl), with alkyl substituents, preferably $C_1$–$C_4$ alkyl (most preferably methyl), hydroxy, or $C_1$–$C_4$ alkylamino (especially —$R^1$NHR$^2$NH2 wherein each $R^1$ and $R^2$ dependently is a $C_1$–$C_3$ alkyl, alkenyl, and/or alkoxy). High refractive index polysiloxanes are available from Dow Corning, Huls America, and General Electric.

When high refractive index silicones are used in the anti-dandruff and conditioning shampoo compositions of the present invention, they are preferably used in solution with a spreading agent, such as a silicone resin or a surfactant, to reduce the surface tension by a sufficient amount to enhance spreading and thereby enhance the glossiness (subsequent to drying) of hair treated with the compositions. Generally, an amount of the spreading agent is used that is sufficient to reduce the surface tension of the high refractive index polysiloxane fluid by at least about 5%, preferably at least about 10%, more preferably at least about 15%, even more preferably at least about 20%, most preferably at least about 25%. Reductions in surface tension of the polysiloxane fluid/spreading agent mixture may improve shine of the hair.

Also, the spreading agent will preferably reduce the surface tension by at least about 2 dynes/cm$^2$, preferably at least about 3 dynes/cm$^2$, even more preferably at least about 4 dynes/cm$^2$, most preferably at least about 5 dynes/cm$^2$.

The surface tension of the mixture of the polysiloxane fluid and the spreading agent, at the proportions present in the final product, is preferably less than or equal to about 30 dynes/cm$^2$, more preferably less than or equal to about 28 dynes/cm$^2$, most preferably less than or equal to about 25 dynes/cm$^2$. Typically, the surface tension will be in the range from about 15 dynes/cm$^2$ to about 30 dynes/cm$^2$, more typically from about 18 dynes/cm$^2$ to about 28 dynes/cm$^2$, and most generally from about 20 dynes/cm$^2$ to about 25 dynes/cm$^2$.

The weight ratio of the highly arylated polysiloxane fluid to the spreading agent will, in general, be from about 1000:1 to about 1:1, preferably from about 100:1 to about 2:1, more preferably from about 50:1 to about 2:1, most preferably from about 25:1 to about 2:1. When fluorinated surfactants are used, particularly high polysiloxane fluid to spreading agent ratios may be effective due to the efficiency of these surfactants. Thus, it is contemplated that ratios significantly above 1000:1 may be used.

Silicone fluids suitable for use in the anti-dandruff and conditioning shampoo compositions of the present invention are disclosed in U.S. Pat. Nos. 2,826,551, 3,964,500, 4,364,837, British Pat. No. 849,433, and *Silicon Compounds*, Petrarch Systems, Inc. (1984), all of which are incorporated herein by reference.

v. Silicone Resins

Silicone resins may be included in the silicone conditioning agent of the anti-dandruff and conditioning shampoo compositions of the present invention. These resins are highly cross-linked polymeric siloxane systems. The cross-linking is introduced through the incorporation of trifunctional and tetrafunctional silanes with monofunctional or difunctional, or both, silanes during manufacture of the silicone resin. As is apparent to one of ordinary skill in the art, the degree of cross-linking that is required in order to result in a silicone resin will vary according to the specific silane units incorporated into the silicone resin. Generally, silicone materials which have a sufficient level of trifunctional and tetrafunctional siloxane monomer units (and hence, a sufficient level of cross-linking) such that they dry down to a rigid, or hard, film are considered to be silicone resins. The ratio of oxygen atoms to silicon atoms is indicative of the level of cross-linking in a particular silicone material. Silicone resins suitable for use in the anti-dandruff and conditioning shampoo compositions of the present invention generally have at least about 1.1 oxygen atoms per silicon atom. Preferably, the ratio of oxygen to silicon atoms is at least about 1.2:1.0. Silanes used in the manufacture of silicone resins include, but are not limited to: monomethyl-, dimethyl-, trimethyl-, monophenyl-, diphenyl-, methylphenyl-, monovinyl-, and methylvinyl-chlorosilanes, and tetra-chlorosilane, with the methyl-substituted silanes being most commonly utilized. Preferred resins are available from General Electric as GE SS4230 and GE SS4267. Commercially available silicone resins are generally supplied in a dissolved form in a low viscosity volatile or non-volatile silicone fluid. The silicone resins for use herein should be supplied and incorporated into the present compositions in such dissolved form, as will be readily apparent to one of ordinary skill in the art.

Silicone materials and silicone resins in particular, can conveniently be identified according to a shorthand nomenclature system known to those of ordinary skill in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{0.5}$; and Q denotes the quadra- or tetra-functional unit $SiO_2$. Primes of the unit symbols (e.g. M', D', T', and Q') denote substituents other than methyl, and must be specifically defined for each occurrence. Typical alternate substituents include, but are not limited to, groups such as vinyl, phenyls, amines, hydroxyls, and the like. The molar ratios of the various units, either in terms of subscripts to the symbols indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or M' in a silicone resin indicates higher levels of cross-linking. As discussed above, however, the overall level of cross-linking can also be indicated by the oxygen to silicon ratio.

Preferred silicone resins for use in the anti-dandruff and conditioning shampoo compositions of the present invention include, but are not limited to MQ, MT, MTQ, MDT and MDTQ resins. Methyl is a preferred silicone substituent. Especially preferred silicone resins are MQ resins, wherein the M:Q ratio is from about 0.5:1.0 to about 1.5:1.0 and the average molecular weight of the silicone resin is from about 1000 to about 10,000.

The weight ratio of the non-volatile silicone fluid, having refractive index below 1.46, to the silicone resin component, when used, is preferably from about 4:1 to about 400:1, more preferably from about 9:1 to about 200:1, most preferably from about 19:1 to about 100:1, particularly when the silicone fluid component is a polydimethylsiloxane fluid or a mixture of polydimethylsiloxane fluid and polydimethylsiloxane gum as described above. Insofar as the silicone resin forms a part of the same phase in the compositions hereof as the silicone fluid, i.e. the conditioning active, the sum of the fluid and resin should be included in determining the level of silicone conditioning agent in the composition.

2. Organic Conditioning Oils

The conditioning component of the anti-dandruff and conditioning shampoo compositions of the present invention may also comprise from about 0.05% to about 3%, by weight of the composition, preferably from about 0.08% to about 1.5%, more preferably from about 0.1% to about 1%, of at least one organic conditioning oil as the conditioning agent, either alone or in combination with other conditioning agents, such as the silicones (described above).

It is believed that these organic conditioning oils provide the shampoo composition with improved conditioning performance when used in combination with the essential components of the composition, and in particular when used in combination with cationic polymers (described below). The conditioning oils may add shine and luster to the hair. Additionally, they may enhance dry combing and dry hair feel. Most or all of these organic conditioning oils are believed to be solubilized in the surfactant micelles of the shampoo composition. It is also believed that this solubilization into the surfactant micelles contributes to the improved hair conditioning performance of the shampoo compositions herein.

The organic conditioning oils suitable for use as the conditioning agent herein are preferably low viscosity, water insoluble, liquids selected from the hydrocarbon oils, polyolefins, fatty esters, and mixtures thereof. The viscosity, as measured at 40° C., of such organic conditioning oils is preferably from about 1 centipoise to about 200 centipoise, more preferably from about 1 centipoise to about 100 centipoise, most preferably from about 2 centipoise to about 50 centipoise.

i. Hydrocarbon Oils

Suitable organic conditioning oils for use as conditioning agents in the anti-dandruff and conditioning shampoo compositions of the present invention include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils preferably are from about $C_{12}$ to about $C_{19}$. Branched chain hydrocarbon oils, including hydrocarbon polymers, typically will contain more than 19 carbon atoms.

Specific non-limiting examples of these hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, polybutene, polydecene, and mixtures thereof. Branched-chain isomers of these compounds, as well as of higher chain length hydrocarbons, can also be used, examples of which include highly branched, saturated or unsaturated, alkanes such as the permethyl-substituted isomers, e.g., the permethyl-substituted isomers of hexadecane and eicosane, such as 2,2,4,4,6,6,8,8-dimethyl-10-methylundecane and 2,2,4,4,6,6-dimethyl-8-methylnonane, available from Permethyl Corporation. Hydrocarbon polymers such as polybutene and polydecene. A preferred hydrocarbon polymer is polybutene, such as the copolymer of isobutylene and butene. A commercially available material of this type is L-14 polybutene from Amoco Chemical Corporation.

ii. Polyolefins

Organic conditioning oils for use in the anti-dandruff and conditioning shampoo compositions of the present invention can also include liquid polyolefins, more preferably liquid poly-α-olefins, most preferably hydrogenated liquid poly-α-olefins. Polyolefins for use herein are prepared by polymerization of $C_4$ to about $C_{14}$ olefenic monomers, preferably from about $C_6$ to about $C_{12}$.

Non-limiting examples of olefenic monomers for use in preparing the polyolefin liquids herein include ethylene, propylene, 1-butene, 1-pentene, 1-hexene, 1-octene, 1-decene, 1-dodecene, 1-tetradecene, branched chain isomers such as 4-methyl-1-pentene, and mixtures thereof. Also suitable for preparing the polyolefin liquids are olefin-containing refinery feedstocks or effluents. Preferred hydrogenated α-olefin monomers include, but are not limited to: 1-hexene to 1-hexadecenes, 1-octene to 1-tetradecene, and mixtures thereof.

iii. Fatty Esters

Other suitable organic conditioning oils for use as the conditioning agent in the anti-dandruff and conditioning shampoo compositions of the present invention include, but are not limited to, fatty esters having at least 10 carbon atoms. These fatty esters include esters with hydrocarbyl chains derived from fatty acids or alcohols (e.g. monoesters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.).

Suitable for use in the anti-dandruff and conditioning shampoo compositions of the present invention are alkyl and alkenyl esters of fatty acids having from about $C_{10}$ to about $C_{22}$ aliphatic chains, and alkyl and alkenyl fatty alcohol carboxylic acid esters having a $C_{10}$ to about $C_{22}$ alkyl and/or alkenyl alcohol-derived aliphatic chain, and mixtures thereof. Specific examples of preferred fatty esters include, but are not limited to: isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Other fatty esters suitable for use in the anti-dandruff and conditioning shampoo compositions of the present invention are mono-carboxylic acid esters of the general formula R'COOR, wherein R' and R are alkyl or alkenyl radicals, and the sum of carbon atoms in R' and R is at least 10, preferably at least 20. The mono-carboxylic acid ester need not necessarily contain at least one chain with at least 10 carbon atoms; rather the total number of aliphatic chain carbon atoms must be least 10. Specific non-limiting examples of mono-carboxylic acid esters include: isopropyl myristate, glycol stearate, and isopropyl laurate.

Still other fatty esters suitable for use in the anti-dandruff and conditioning shampoo compositions of the present invention are di- and tri-alkyl and alkenyl esters of carboxylic acids, such as esters of $C_4$ to $C_8$ dicarboxylic acids (e.g. $C_1$, to $C_{22}$ esters, preferably $C_1$ to $C_6$, of succinic acid, glutaric acid, adipic acid, hexanoic acid, heptanoic acid, and octanoic acid). Specific non-limiting examples of di- and tri-alkyl and alkenyl esters of carboxylic acids include isocetyl stearoyl stearate, diisopropyl adipate, and tristearyl citrate.

Other fatty esters suitable for use in the anti-dandruff and conditioning shampoo compositions of the present invention are those known as polyhydric alcohol esters. Such polyhydric alcohol esters include alkylene glycol esters, such as ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Still other fatty esters suitable for use in the anti-dandruff and conditioning shampoo compositions of the present invention are glycerides, including, but not limited to, mono-, di-, and tri-glycerides, preferably di- and tri-glycerides, most preferably triglycerides. For use in the shampoo compositions described herein, the glycerides are preferably the mono-, di-, and tri-esters of glycerol and long chain carboxylic acids, such as $C_{10}$ to $C_{22}$ carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include, but are not limited to, triolein and tristearin glyceryl dilaurate.

Other fatty esters suitable for use in the anti-dandruff and conditioning shampoo compositions of the present invention are water insoluble synthetic fatty esters. Some preferred synthetic esters conform to the general Formula (IX):

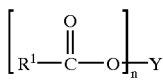

wherein $R^1$ is a $C_7$ to $C_9$ alkyl, alkenyl, hydroxyalkyl or hydroxyalkenyl group, preferably a saturated alkyl group, more preferably a saturated, linear, alkyl group; n is a positive integer having a value from 2 to 4, preferably 3; and Y is an alkyl, alkenyl, hydroxy or carboxy substituted alkyl or alkenyl, having from about 2 to about 20 carbon atoms, preferably from about 3 to about 14 carbon atoms. Other preferred synthetic esters conform to the general Formula (X):

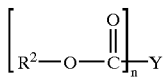

wherein $R^2$ is a $C_8$ to $C_{10}$ alkyl, alkenyl, hydroxyalkyl or hydroxyalkenyl group; preferably a saturated alkyl group, more preferably a saturated, linear, alkyl group; n and Y are as defined above in Formula (X).

It is believed that the preferred synthetic esters provide improved wet hair feel when used in combination with the essential components of the shampoo compositions of the present invention, particularly when used in combination with the cationic polymer component (described below). These synthetic esters improve wet hair feel by reducing the slimy or excessively conditioned feel of wet hair that has been conditioned by a cationic polymer.

Specific non-limiting examples of suitable synthetic fatty esters for use in the anti-dandruff and conditioning shampoo compositions of the present invention include: P-43 ($C_8$–$C_{10}$ triester of trimethylolpropane), MCP-684 (tetraester of 3,3 diethanol-1,5 pentadiol), MCP 121 ($C_8$–$C_{10}$ diester of adipic acid), all of which are available from Mobil Chemical Company.

3. Other Conditioning Agents

Also suitable for use in the compositions herein are the conditioning agents described by the Procter & Gamble Company in U.S. Pat. Nos. 5,674,478, and 5,750,122, both of which are incorporated herein in their entirety by reference. Also suitable for use herein are those conditioning agents described in U.S. Pat. No. 4,529,586 (Clairol), U.S. Pat. No. 4,507,280 (Clairol), U.S. Pat. No. 4,663,158 (Clairol), U.S. Pat. No. 4,197,865 (L'Oreal), U.S. Pat. No. 4,217,914 (L'Oreal), U.S. Pat. No. 4,381,919 (L'Oreal), and U.S. Pat. No. 4,422,853 (L'Oreal), all of which descriptions are incorporated herein by reference.

Some other preferred silicone conditioning agents for use in the compositions of the present invention include: Abil® S 201 (dimethicone/sodium PG-propyldimethicone thiosulfate copolymer), available from Goldschmidt; DC Q2-8220 (trimethylsilyl amodimethicone) available from Dow Corning; DC 949 (amodimethicone, cetrimonium chloride, and Trideceth-12), available from Dow Corning; DC 749 (cyclomethicone and trimethylsiloxysilicate), available from Dow Corning; DC2502 (cetyl dimethicone), available from Dow Corning; BC97/004 and BC 99/088 (amino functionalized silicone microemulsions), available from Basildon Chemicals; GE SME253 and SM2115-D2 and SM2658 and SF1708 (amino functionalized silicone microemulsions), available from General Electric; siliconized meadowfoam seed oil, available from Croda; and those silicone conditioning agents described by GAF Corp. in U.S. Pat. No. 4,834,767 (quaternized amino lactam), by Biosil Technologies in U.S. Pat. No. 5,854,319 (reactive silicone emulsions containing amino acids), and by Dow Corning in U.S. Pat. No. 4,898,585 (polysiloxanes), all of which descriptions are incorporated herein by reference.

5 C. Anti-dandruff Particulate

The anti-dandruff and conditioning shampoo compositions of the present invention comprise from about 0.1% to about 4%, by weight of the composition, preferably from about 0.1% to about 3%, most preferably from about 0.3% to about 2%, of an anti-dandruff particulate suitable for application to the hair or skin. The anti-dandruff particulate provides the shampoo compositions with anti-microbial activity. Suitable, non-limiting examples of anti-dandruff particulates include: pyridinethione salts, selenium sulfide, particulate sulfur, and mixtures thereof. Preferred are pyridinethione salts. Such anti-dandruff particulate should be physically and chemically compatible with the essential components of the composition, and should not otherwise unduly impair product stability, aesthetics or performance.

1. Pyridinethione Salts

Pyridinethione anti-dandruff particulates, especially 1-hydroxy-2-pyridinethione salts, are highly preferred particulate anti-dandruff agents for use in the anti-dandruff and conditioning shampoo compositions of the present invention. The concentration of pyridinethione anti-dandruff particulate typically ranges from about 0.1% to about 4%, by weight of the composition, preferably from about 0.1% to about 3%, most preferably from about 0.3% to about 2%. Preferred pyridinethione salts include those formed from heavy metals such as zinc, tin, cadmium, magnesium, aluminum and zirconium, preferably zinc, more preferably the zinc salt of 1-hydroxy-2-pyridinethione (known as "zinc pyridinethione" or "ZPT"), most preferably 1-hydroxy-2-pyridinethione salts in platelet particle form, wherein the particles have an average size of up to about $20\mu$, preferably up to about $5\mu$, most preferably up to about $2.5\mu$. Salts formed from other cations, such as sodium, may also be suitable. Pyridinethione anti-dandruff agents are described, for example, in U.S. Pat. Nos. 2,809,971; 3,236,733; 3,753, 196; 3,761,418; 4,345,080; 4,323,683; 4,379,753; and 4,470,982, all of which are incorporated herein by reference.

It is contemplated that when ZPT is used as the anti-dandruff particulate in the shampoo compositions herein, that the growth or re-growth of hair may be stimulated or regulated, or both, or that hair loss may be reduced or inhibited, or that hair may appear thicker or fuller.

2. Selenium Sulfide

Selenium sulfide is a particulate anti-dandruff agent suitable for use in the anti-dandruff and conditioning shampoo compositions of the present invention, effective concentrations of which range from about 0.1% to about 4%, by weight of the composition, preferably from about 0.3% to about 2.5%, more preferably from about 0.5% to about 1.5%. Selenium sulfide is generally regarded as a compound having one mole of selenium and two moles of sulfur, although it may also be a cyclic structure that conforms to the general formula $Se_xS_y$, wherein x+y=8. Average particle diameters for the selenium sulfide are typically less than 15 $\mu$m, as measured by forward laser light scattering device (e.g. Malvern 3600 instrument), preferably less than 10 $\mu$m. Selenium sulfide compounds are described, for example, in U.S. Pat. Nos. 2,694,668; 3,152,046; 4,089,945; and 4,885,107, all of which descriptions are incorporated herein by reference.

3. Sulfur

Sulfur may also be used as the particulate anti-dandruff agent in the anti-dandruff and conditioning shampoo compositions of the present invention. Effective concentrations of the 10 particulate sulfur are typically from about 1% to about 4%, by weight of the composition, preferably from about 2% to about 4%.

D. Cationic Polymer

The anti-dandruff and conditioning shampoo compositions of the present invention comprise from about 0.02% to about 5%, by weight of the composition, preferably from about 0.05% to about 3%, more preferably from about 0.1% to about 2%, most preferably from about 0.5% to about 1%, of at least one organic, cationic deposition and conditioning polymer suitable for application to the hair or skin. The cationic polymers are believed to provide increased anti-dandruff efficacy and increased conditioning to the shampoo compositions described herein. Such cationic polymers should be physically and chemically compatible with the essential components described herein, and should not otherwise unduly impair product stability, aesthetics or performance.

1. Characteristics of the Cationic Polymers

The cationic polymers useful in the present invention must be selected and must be present at a level such that the cationic polymers are soluble in the shampoo composition, and which are preferably soluble in a complex coacervate phase in the shampoo composition, upon dilution. Such coacervate is described in detail below. Also, physical properties of the cationic polymers and suitable counterions are detailed.

i. Coacervate Formed from Cationic Polymer

A coacervate is formed, upon dilution of the shampoo composition, between the cationic polymer and the anionic detersive surfactant component (described above) of the present invention. It is believed that the cationic moiety of the polymer binds with the anionic moiety of the surfactant to form an insoluble complex that precipitates, upon dilution (the coacervate). Complex coacervates of the cationic polymer can also be formed with other optional anionic components of the shampoo composition (described below). Coacervate formation is dependent upon a variety of criteria, such as molecular weight, component concentration, and ratio of interacting ionic components, ionic strength (including modification of ionic strength, for example, by addition of salts), charge density of the cationic and anionic components, pH, and temperature. Coacervate systems and the effect of these parameters have been described, for example, in J. Caelles, et al., "Anionic and Cationic Compounds in Mixed Systems", Cosmetics & Toiletries, vol. 106, (April 1991), pp 49–54; C. J. van Oss, "Coacervation, Complex-Coacervation and Flocculation", J. Dispersion Science and Tech., vol. 9 (5,6), (1988–89), pp 561–73; and in D. J. Burgess, "Practical Analysis of Complex Coacervate Systems", J. of Colloid and Interface Science, vol. 140, no. 1, (November 1990), pp 227–38; all of which descriptions are incorporated herein by reference. The shampoo compositions described herein, typically have a ratio of anionic detersive surfactant component to cationic polymer component from about 25:0.02 to about 1:5, preferably from about 20:0.1 to about 12:1.

Coacervates are believed to provide conditioning benefits, especially conditioning benefits during product use when the hair is wet, by helping to deposit conditioning agents onto the hair and scalp. Coacervates are also known in the art to aid deposition of other types of particulates. This is thought to occur by concentrating particulates within coacervate boundaries upon dilution.

It has also been found that the characteristics of polymer in such compositions can affect the bioavailability/coverage of anti-dandruff particulates, such characteristics include cationic guar polymer molecular weight and charge density. Guars with lower molecular weight are preferred, guars with lower charge density are preferred. Guars with lower molecular weight and lower charge density are highly preferred. It is believed that these select guars impart modified physical properties (i.e. rheology) to the coacervates formed.

Techniques for analysis of formation of complex coacervates are known in the art. For example, microscopic analyses of the shampoo compositions, at any chosen stage of dilution, can be utilized to identify whether a coacervate phase has formed. Such coacervate phase will be identifiable as an additional emulsified phase in the composition. The use of dyes can aid in distinguishing the coacervate phase from other insoluble phases dispersed in the shampoo composition.

ii. Physical Properties of the Cationic Polymer

The average molecular weight of cationic conditioning polymers suitable for use herein is typically from about 5,000 to about 10,000,000, preferably from about 100,000 to about 2,000,000, more preferably from about 200,000 to about 1,500,000, more preferably from about 250,000 to about 850,000, more preferably from about 350,000 to about 850,000, most preferably from about 350,000 to about 500,000. The polymers have a cationic charge density typically from about 0.2 meq/g to about 7 meq/g, as measured at the pH of intended use of the shampoo composition, preferably from about 0.4 meq/gm to about 5 meq/g, more preferably from about 0.6 meq/g to about 2 meq/g, more preferably from about 0.5 meq/g to about 0.1 meq/g, more preferably from about 0.5 meq/g to about 0.9 meq/g. The pH of intended use of the shampoo composition typically ranges from about pH 3 to about pH 9, preferably from about pH 4 to about pH 7.

iii. Counterions Used in Forming Cationic Polymer

Any anionic counterions may be use in association with the cationic polymers so long as the cationic polymers remain soluble in water, in the shampoo composition, or in a coacervate phase of the shampoo composition, and so long as the counterions are physically and chemically compatible with the essential components of the shampoo composition or do not otherwise unduly impair product performance, stability or aesthetics. Non-limiting examples of such counterions include: halides (e.g., chloride, fluoride, bromide, iodide), sulfate, methylsulfate, and mixtures thereof.

2. Types Cationic Polymers

Examples of cationic polymers which may be suitably employed in the shampoo compositions herein include, but are not limited to cationic polysaccharides (e.g. cationic cellulose derivatives and cationic guars), copolymers of vinyl monomers, vinyl pyrrolidone copolymers, cationic modified proteins, and certain polymeric quaternary salts. Such cationic polymers are described in detail below.

i. Cationic Polysaccharides

Preferred cationic polymers for use in the anti-dandruff and conditioning shampoo compositions of the present invention are those known as cationic polysaccharides. Cationic polysaccharides are those polymers based on $C_5$ to $C_6$ sugars and derivatives which have been made cationic by engrafting of cationic moieties on the polysaccharide backbone, and include homopolymers, copolymers, terpolymers, and so forth, of quaternary ammonium or cationic amine-substituted monomer units, optionally in combination with non-cationic monomers. The polysaccharides may be composed of one type of sugar or of more than one type. The cationic amines can be primary, secondary, or tertiary amines (preferably secondary or tertiary), depending upon the particular species and the selected pH of the shampoo composition. The monomers may be in straight chain or branched chain geometric arrangements. All of the monomer units may have cationic nitrogen-containing moieties attached thereto, preferably some of the monomer units do not have such moieties attached. Non-limiting examples of cationic polysaccharides are described in the *CTFA Cosmetic Ingredient Dictionary*, 3d ed., edited by Estrin, Crosley, and Haynes, (The Cosmetic, Toiletry, and Fragrance Association, Inc., Washington, D.C. (1982), which description is incorporated herein by reference.

Cationic polysaccharide polymers include the following: cationic celluloses and hydroxyethylcelluloses; cationic starches and hydroxyalkyl starches; cationic polymers based on the galactomannan copolymer known as guar gum obtained from the endosperm of the guar bean; cationic polymers based on arabinose vegetable gums; cationic polymers derived from xylose polymers (such as those found in wood, straw, cottonseed hulls, and corn cobs); cationic polymers derived from fucose polymers (such as those found as a component of cell walls in seaweed); cationic polymers derived from fructose polymers (such as Inulin, which is found in certain plants); cationic polymers based on acid-containing sugars (such as galacturonic acid and glucouronic acid); cationic polymers based on amine sugars (such as galactosamine and glucosamine); cationic polymers based on 5 and 6 member ring polyalcohols; cationic polymers based on galactose monomers (such as those found in plant gums and mucilates); and cationic polymers based on mannose monomers (such as those found in plants, yeasts, and red algae). Preferred are cationic celluloses and hydroxyethylcelluloses; cationic starches and hydroxyalkyl starches; cationic polymers based on guar gum, and mixtures thereof.

a. Cationic Cellulose Derivatives

Suitable polysaccharide cationic polymers for use in the anti-dandruff and conditioning shampoo compositions of the present invention are the cationic cellulose derivatives and cationic starch derivatives. Such cationic polymers include those which conform to the general Formula (XI):

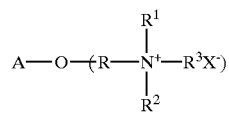

wherein A is an anhydroglucose residual group (e.g. a starch or cellulose anhydroglucose residual); R is an alkylene oxyalkylene, polyoxyalkylene, or hydroxyalkylene group, or combination thereof; $R^1$, $R^2$, and $R^3$ are independently alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$, and $R^3$) preferably being about 20 or less; and X is an anionic counterion as described above.

Preferred cationic cellulose polymers include, but are not limited to, those polymers available from Amerchol Corporation, in their Polymer JR and LR series of polymers, as salts of hydroxyethyl cellulose reacted with trimethyl ammonium substituted epoxide, known in the industry (CTFA) as Polyquaternium 10 (e.g. JR 30M®, available from Amerchol Corporation). Preferred Polyquaternium 10 polymers for use herein, typically have a charge density from about 0.3 meq/g to about 3 meq/g and a molecular weight from about 200,000 to about 1,500,00. Another non-limiting of a preferred type of cationic cellulose includes the polymeric quaternary ammonium salt of hydroxyethyl cellulose reacted with lauryl dimethyl ammonium-substituted epoxide, known in the industry (CTFA) as Polyquaternium 24, (e.g. Polymer LM 200®, available from Amerchol Corporation).

Also suitable for use herein are those quaternary nitrogen-containing cellulose copolymers of hydroxyethylcellulose reacted with diallyldimethyl ammonium chloride, known in the industry (CTFA) as Polyquaternium 4 (e.g. Celquat® H-100, available from National Starch Corporation). Quaternary nitrogen-containing cellulose ethers suitable for use herein are described in U.S. Pat. No. 3,962,418, and still other copolymers of etherified cellulose and starch suitable for use herein are described in U.S. Pat. No. 3,958,581, both of which descriptions are incorporated herein by reference.

b. Cationic Guars

Other suitable polysaccharide cationic polymers for use in the anti-dandruff and conditioning shampoo compositions of the present invention are cationic guar polymers. Guars are cationically substituted galactomannan (guar) gum derivatives. The molecular weight of such derivatives ranges typically from about 50,000 to about 2,500,000, preferably from about 50,000 to about 1,000,000, more preferably from about 50,000 to about 700,000.

Guar gum for use in preparing these guar gum derivatives is typically obtained as a naturally occurring material from the seeds of the guar plant. The guar molecule itself is a straight chain mannan branched at regular intervals with single membered galactose units on alternative mannose units. The mannose units are linked to each other by means of β (1–4) glycosidic linkages. The galactose branching arises by way of an α (1–6) linkage. Cationic derivatives of the guar gums are obtained by reaction between the hydroxyl groups of the polygalactomannan and reactive quaternary ammonium compounds. The degree of substitution of the cationic groups onto the guar structure must be sufficient to provide the requisite cationic charge density described above.

Suitable quaternary ammonium compounds for use in forming the cationic guar polymers include those conforming to the general Formula (XII):

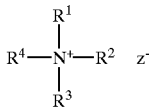

wherein where $R^1$, $R^2$ and $R^3$ are methyl or ethyl groups; $R^4$ is either an epoxyalkyl group of the general Formula (XIII):

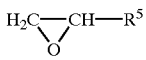

or $R^4$ is a halohydrin group of the general Formula (XIV):

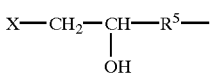

wherein $R^5$ is a $C_1$ to $C_3$ alkylene; X is chlorine or bromine, and Z is an anion such as $Cl^-$, $Br^-$, $I^-$ or $HSO_4^-$.

Cationic guar polymers (cationic derivatives of guar gum) formed from the reagents described above are represented by the general Formula (XV):

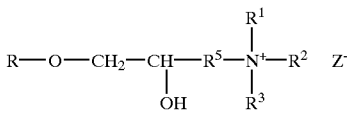

wherein R is guar gum. Preferably, the cationic guar polymer is guar hydroxypropyltrimethylammonium chloride, which can be more specifically represented by the general Formula (XVI):

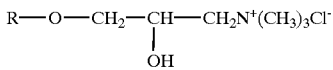

Specific non-limiting examples of cationic guar polymers which conform to Formula XVI include: Jaguar® C 13S, having a cationic charge density of 0.8 meq/g (available from Rhodia Company) and Jaguar® C 17, having a cationic charge density of 1.6 meq/g (available from Rhodia Company). Other suitable cationic guar polymers include hydroxypropylated cationic guar derivatives. Still other suitable cationic polymers include copolymers of etherified guar, some examples of which are described in U.S. Pat. No. 3,958,581, which description is incorporated herein by reference.

ii. Copolymers of Vinyl Monomers

Other suitable cationic polymers for use in the anti-dandruff and conditioning shampoo compositions of the present invention are copolymers of vinyl monomers, having cationic protonated amine or quaternary ammonium functionalities, reacted with water soluble monomers. Non-limiting examples of such monomers include: acrylamide, methacrylamide, alkyl and dialkyl acrylamides, alkyl and dialkyl methacrylamides, alkyl acrylate, alkyl methacrylate, vinyl caprolactone, vinyl pyrrolidone, and mixtures thereof. The alkyl and dialkyl substituted monomers preferably have from $C_1$ to $C_7$ alkyl groups, more preferably from $C_1$ to $C_3$ alkyl groups. Other suitable monomers include vinyl esters, vinyl alcohol (made by hydrolysis of polyvinyl acetate), maleic anhydride, propylene glycol, ethylene glycol, and mixtures thereof.

Suitable cationic protonated amino and quaternary ammonium monomers, for inclusion in the cationic polymers of the shampoo composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts; and vinyl quaternary ammonium monomers having cyclic cationic nitrogen-containing rings such as pyridinium, imidazolium, and quaternized pyrrolidones, such as alkyl vinyl imidazolium, alkyl vinyl pyridinium, and alkyl vinyl pyrrolidone salts. The alkyl portions of these monomers are preferably lower alkyls such as the $C_1$-$C_3$ alkyls.

Suitable amine-substituted vinyl monomers for use herein include, dialkylaminoalkyl acrylamide, and dialkylaminoalkyl methacrylamide, wherein the alkyl groups are preferably $C_1$ to $C_7$ hydrocarbyls, more preferably $C_1$ to $C_3$ alkyls.

iii. Vinyl Pyrrolidone Copolymers

Other suitable cationic polymers for use in the anti-dandruff and conditioning shampoo compositions of the present invention include: copolymers of 1-vinyl-2-pyrrolidone and 1-vinyl-3-methylimidazolium salt (e.g., chloride salt), known in the industry (CTFA) as Polyquaternium 16 (e.g. Luviquat® FC 370, available from BASF Wyandotte Corporation); copolymers of 1-vinyl-2-pyrrolidone and dimethylaminoethyl methacrylate, known in the industry (CTFA) as Polyquaternium 11 (e.g. Gafquat® 755N, available from ISP Corporation); cationic diallyl quaternary ammonium-containing polymers, including, for example, dimethyldiallylammonium chloride homopolymer, known in the industry (CTFA) as Polyquaternium 6; copolymers of acrylamide and dimethyldiallylammonium chloride, known in the industry (CTFA) as Polyquaternium 7; and mineral acid salts of amino-alkyl esters of homopolymers and copolymers of unsaturated $C_3$ to $C_5$ carboxylic acids, such as those described in U.S. Pat. No. 4,009,256, which description is incorporated herein by reference.

iv. Cationic Modified Proteins and Polymeric Quaternary Salts

Still other cationic polymers for use in the anti-dandruff and conditioning shampoo compositions of the present invention are cationic modified proteins, such as lauryldimonium hydroxypropyl collagen (e.g. Croquat® L, available from Croda Corporation), or cocodimonium hydroxypropyl hydrolized hair keratin (e.g. Croquat® HH, available from Croda Corporation). Other cationic polymers include the polymeric quaternary salt prepared the reaction of adipic acid and dimethylaminopropylamine, reacted with dichloroethyl ether, known in the industry (CTFA) as Polyquaternium 2 (e.g. Mirapol® AD-1, available from Rhodia), and the polymeric quaternary salt prepared by the reaction of azelaic acid and dimethylaminopropylether, known in the industry (CTFA) as Polyquaternium 18 (e.g. Mirapol(® AZ-1, available from Rhodia Corporation).

v. Other Cationic Polymers

Yet other cationic polymers suitable for use herein are the Arquad® series of quaternary ammonium salts, available from Akzo Nobel. Other preferred cationic polymers for use herein include: Polymer KG30M (polyquaternium 10 and quaternized cellulose), Incroquat® behenyl trimonium methosulfate (cetearyl alcohol and behentrimonium methosulfate), available from Croda; Merquat® 5 (quaternary ammonium resin), available from Calgon;

Gafquat® series 440 (cationic quaternized copolymers), available from ISP; Akypoquat® 131, available from Kao; Salcare® SC 60 (quaternary ammonium resin), or Salcare® SC95 or SC96 (cationic liquid dispersion thickeners), all available from Ciba; and Meadowquat® HG (PEG-2-dimeadowfoamamido-ethylmonium methosulfate), available from Fanning.

E. Polyalkylene Glycol

The anti-dandruff and conditioning shampoo compositions of the present invention comprise from about 0.005% to about 1.5%, by weight of the composition preferably from about 0.025% to about 0.1%, more preferably from about 0.05% to about 1%, more preferably from about 0.1% to about 0.5%, most preferably from about 0.1% to about 0.3%, of selected polyalkylene glycols suitable for application to the hair or skin. The select polyalkylene glycols are believed to provide enhanced lather performance, improved shampoo spreadability, and importantly, increased anti-dandruff particulate efficacy to the compositions described herein. Such polyalkylene glycols should be physically and chemically compatible with the essential components described herein, and should not otherwise unduly impair product stability, aesthetics, or performance.

It has been found that these polyalkylene glycols, when added to the shampoo compositions described herein, enhance lather performance by delivering a richer, denser lather which correlates with consumer perception of hair conditioning performance. It has also been found that, in those embodiments which contain silicone conditioning agents, the selected polyalkylene glycols can reduce the concentration of anionic detersive surfactant necessary to provide hair cleaning. In such reduced-surfactant compositions, hair cleansing and conditioning performance remains good, while overall lather performance is enhanced. Polyethylene glycols, for example, are known for use in improving lather performance in cleansing compositions, as described in U.S. Pat. No. 5,837,661, which description is incorporated herein by reference.

It has also been found that these selected polyalkylene glycols, when added to a silicone-containing shampoo composition, enhance spreadability of the shampoo compositions in hair. Enhanced spreading of the shampoo composition during application also provides consumers with a perception of enhanced conditioning performance. This performance is especially surprising from these selected polyalkylene glycols which are known thickening agents, and as thickening agents would be expected to impair rather than enhance spreadability of the shampoo compositions into hair.

The polyalkylene glycols suitable for use in the shampoo compositions herein are characterized by the general Formula (XVII):

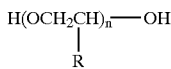

wherein R is hydrogen, methyl, or mixtures thereof, preferably hydrogen, and n is an integer having an average value from about 1,500 to about 120,000, preferably from about 1,500 to about 50,000, more preferably from about 2,500 to about 25,000, and most preferably from about 3,500 to about 15,000. When R is hydrogen, these materials are polymers of ethylene oxide, which are also known as polyethylene glycols. When R is methyl, these materials are polymers of propylene oxide, which are also known as polypropylene glycols. When R is methyl, it is also understood that various positional isomers of the resulting polymers can exist. Preferred for use herein are polyethylene glycols, polypropylene glycols, and mixtures thereof.

Specific non-limiting examples of polyethylene glycol polymers for use in the anti-dandruff and conditioning shampoo compositions of the present invention include: PEG 2M, wherein R is hydrogen and n has an average value of about 2,000 (e.g. Polyox WSR® N-10, available from Union Carbide); PEG 5M, wherein R is hydrogen and n has an average value of about 5,000 (e.g. Polyox WSR® N-35 and Polyox WSR® N-80, both available from Union Carbide); PEG 7M, wherein R is hydrogen and n has an average value of about 7,000 (e.g. Polyox WSR® N-750, available from Union Carbide); PEG 9M, wherein R is hydrogen and n has an average value of about 9,000 (e.g. Polyox WSR® N-3333, available from Union Carbide); PEG 14 M, wherein R is hydrogen and n has an average value of about 14,000 (e.g. Polyox WSR® N-3000, available from Union Carbide); PEG 23M, wherein R is hydrogen and n has an average value of about 23,000 (e.g. Polyox WSR® N-12k, available from Union Carbide); PEG 90M, wherein R is hydrogen and n has an average value of about 90,000 (e.g. Polyox WSR® 301, available from Union Carbide); and PEG 100M, wherein R is hydrogen and n has an average value of about 100,000 (e.g. Carbowax PEG 4600™, available from Union Carbide). Preferred polyethylene glycols include PEG 7M, PEG 14M, PEG 25M, PEG 90M, and mixtures thereof.

F. Water

The anti-dandruff and conditioning shampoo compositions of the present invention comprise from about 20% to about 94.75%, by weight of the composition, preferably from about 50% to about 94.75%, more preferably from about 60% to about 85%, of water.

II. Optional Components

The anti-dandruff and conditioning shampoo compositions of the present invention may, in some embodiments, further comprise additional optional components known or otherwise effective for use in hair care or personal care products. Additional surfactants, suspending agents, hair growth regulating agents, and other optional components are described in detail below.

A. Other Surfactants

The anti-dandruff and conditioning shampoo compositions of the present invention may, in some embodiments, further comprise from about 0.5% to about 25%, by weight of the composition, preferably from about 1% to about 20%, most preferably from about 1% to about 10%, of a surfactant other than the anionic surfactants described above, suitable for application to the hair or skin. Such optional other surfactants should be chemically and physically compatible with the essential components of the shampoo composition, and should not otherwise unduly impair product performance, aesthetics or stability. Suitable other surfactants include, but are not limited to: amphoteric, zwitterionic, cationic, nonionic and mixtures thereof.

Amphoteric detersive surfactants suitable for use herein include, but are not limited to, those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group such as carboxy, sulfonate, sulfate, phosphate, or phosphonate.

Zwitterionic detersive surfactants suitable for use herein include, but are not limited to, those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Preferred zwitterionic detersive surfactants are the betaines.

Cationic detersive surfactants suitable for use herein include, but are not limited to, surfactants containing quaternary nitrogen moieties. Examples of suitable cationic surfactants are those corresponding to the general Formula (XVIII):

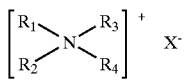

wherein $R_1$, $R_2$, $R_3$, and $R_4$ are independently selected from a $C_1$ to $C_{22}$ aliphatic group or an aromatic, alkoxy, polyoxyalkylene, alkylamido, hydroxyalkyl, aryl or alkylaryl group having up to about 22 carbon atoms, preferably $C_1$ to $C_{22}$ alkyl; and X is a salt-forming anion, such as those selected from halogen (e.g. chloride, bromide), acetate, citrate, lactate, glycolate, phosphate nitrate, sulfate, and alkylsulfate radicals. The aliphatic groups can contain, in addition to carbon and hydrogen atoms, ether linkages, and other groups, such as amino groups. The longer chain (e.g. $C_{12}$ and higher) aliphatic groups can be saturated or unsaturated.

Preferred cationic detersive surfactants are those containing two long alkyl chains and two short alkyl chains or those containing one long alkyl chain and three short alkyl chains. Such long alkyl chains are preferably from $C_{12}$ to $C_{22}$, more preferably from $C_{16}$ to $C_{22}$. Such short alkyl chains are preferably from $C_1$ to $C_3$, more preferably from $C_1$ to $C_2$.

Nonionic detersive surfactants suitable for use herein include, but are not limited to, those compounds produced by condensation of alkylene oxide groups (hydrophilic in nature) with an organic hydrophobic compound, which may be aliphatic or alkyl aromatic in nature.

Non-limiting examples of other amphoteric, zwitterionic, cationic and nonionic detersive surfactants suitable for use in the anti-dandruff and conditioning shampoo composition of the present invention are described in McCutcheon's, Emulsifiers and Detergents, (1989), published by M.C. Pub. Co., and in U.S. Pat. No. 2,438,091; U.S. Pat. No. 2,528,378; U.S. Pat. No. 2,658,072; U.S. Pat. No. 3,155,591; U.S. Pat. No. 3,929,678; U.S. Pat. No. 3,959,461; U.S. Pat. No. 4,387,090; U.S. Pat. No. 5,104,646; U.S. Pat. No. 5,106,609; and U.S. Pat. No. 5,837,661, all of which descriptions are incorporated herein by reference.

B. Suspending Agent

The anti-dandruff and conditioning shampoo compositions of the present invention may, in some embodiments, comprise from about 0.1% to about 10%, by weight of the composition, preferably from about 0.3% to about 5%, more preferably from about 0.3% to about 2.5%, of a suspending agent suitable for application to the hair or skin. It is believed that the suspending agent suspends water-insoluble, dispersed materials in the shampoo compositions. Such suspending agent should be physically and chemically compatible with the essential components of the composition, and should not otherwise unduly impair product stability, aesthetics or performance. Examples of suspending agents which may be suitably employed in the shampoo compositions herein include, but are not limited to: acyl derivatives, long chain amine oxides, xanthan gum, and mixtures thereof. These and other suitable suspending agents are described in further detail below.

1. Acyl Derivatives and Long Chain Amine Oxides

Acyl derivative suspending agents include, but are not limited to: glyceryl esters, long chain hydrocarbyls, long chain esters of long chain fatty acids, long chain esters of long chain alkanol amides. Another suitable suspending agent group includes the long chain amine oxides. Acyl derivative and long chain amine oxide suspending agents are described in U.S. Pat. No. 4,741,855, which description is incorporated herein by reference.

Preferred acyl derivative suspending agents for use herein are glyceryl esters, which include $C_{16}$ to $C_{22}$ ethylene glycol esters of fatty acids. More preferred are the ethylene glycol stearates, both mono- and di-stearate, most preferred is ethylene glycol di-stearate containing less than about 7% of the mono-stearate.

Also suitable for use in the shampoo compositions herein are long chain (i.e. $C_8$ to $C_{22}$) hydrocarbyls, which include N,N-dihydrocarbyl amido benzoic acid and soluble salts thereof (e.g., Na, K), particularly N,N-di-(hydrogenated) $C_{16}$, $C_{18}$ and tallow amido benzoic acid species of this family, available from Stepan Company. Non-limiting examples of long chain esters of long chain fatty acids include: stearyl stearate and cetyl palmitate. Non-limiting examples of long chain esters of long chain alkanol amides include: stearamide diethanolamide distearate and stearamide monoethanolamide stearate. Non-limiting examples of suitable long chain amine oxides for use as suspending agents herein include the alkyl ($C_{16}$–$C_{22}$) dimethyl amine oxides (e.g. stearyl dimethyl amine oxide).

2. Xanthan Gum

Also suitable as a suspending agent herein is xanthan gum. The concentration of xanthan gum will typically range from about 0.1% to about 3%, by weight of the composition, preferably from about 0.4% to about 1.2%. The use of xanthan gum as a suspending agent in silicone containing shampoo compositions is described, for example, in U.S. Pat. No. 4,788,006, which description is incorporated herein by reference. Combinations of long chain acyl derivatives and xanthan gum may also be used as a suspending agent in the shampoo compositions, as is described in U.S. Pat. No. 4,704,272, which description is incorporated herein by reference.

3. Other Suspending Agents

Still other suitable suspending agents for use in the anti-dandruff and conditioning shampoo compositions of the present invention include carboxyvinyl polymers. Preferred among these polymers are the copolymers of acrylic acid crosslinked with polyallylsucrose, as described in U.S. Pat. No. 2,798,053, which description is incorporated herein by reference. Examples of these polymers include Carbopol 934, 940, 941, and 956, available from B.F. Goodrich Company.

Other suitable suspending agents for use herein include primary amines having a fatty alkyl moiety having at least about 16 carbon atoms (e.g. palmitamine, and stearamine), and secondary amines having two fatty alkyl moieties each having at least about 12 carbon atoms (e.g. dipalmitoylamine, and di-(hydrogenated tallow)-amine). Also suitable are di-(hydrogenated tallow)-phthalic acid amide, and cross-linked maleic anhydride-methyl vinyl ether copolymer.

Still other suitable suspending agents may be used in the shampoo compositions, including those that can impart a gel-like viscosity to the composition, such as water soluble or colloidally water soluble polymers like cellulose ethers (e.g., methylcellulose, hydroxybutyl methylcellulose, hydroxypropylcellulose, hydroxypropyl methylcellulose, hydroxyethyl ethylcellulose and hydroxyethylcellulose), guar gum, polyvinyl alcohol, polyvinyl pyrrolidone, hydroxypropyl guar gum, starch and starch derivatives, and other thickeners, viscosity modifiers, gelling agents, and mixtures thereof. A preferred viscosity modifier useful as a suspending agent is trihydroxystearin, (e.g. Thixin R™, available from Rheox Company).

C. Hair Growth Regulating Agents

The compositions herein may also optionally comprise, in addition to zinc pyrithione, other hair growth regulating agents. Such agents can be chosen from a wide variety of molecules which can function in different ways to enhance the hair growth effects of a compound of the present invention. These optional agents, when present, are typically employed in the compositions herein at a level ranging from about 0.001% to about 15%, preferably from about 0.1% to about 10%, most preferably from about 0.5% to about 5% by weight of the composition.

As used herein, the term "hair growth regulating" is meant to include: stimulating hair growth and/or hair thickening; preventing, reducing, arresting and/or retarding the loss of hair and/or the thinning of hair; increasing the rate of hair growth; inducing the formation of a greater number of hair strands; increasing the diameter of the hair strand; lengthening the hair strand; changing the hair follicle from vellus to terminal; converting follicles from telogen to anagen phase (thereby increasing the overall ratio of anagen phase follicles relative to telogen phase follicles); treating alopecias; and any combination thereof.

Vasodilators such as potassium channel agonists including, for example, minoxidil and minoxidil derivatives such as aminexil and such as those described in U.S. Pat. Nos. 3,382,247, 5,756,092, issued May 26, 1998, U.S. Pat. No. 5,772,990, issued Jun. 30, 1998, U.S. Pat. No. 5,760,043, issued Jun. 2, 1998, U.S. Pat. No. 328,914, issued Jul. 12, 1994, U.S. Pat. No. 5,466,694, issued Nov. 14, 1995, 5,438,058, issued Aug. 1, 1995, and U.S. Pat. No. 4,973,474, issued Nov. 27, 1990, (all of which are herein incorporated by reference), and cromakalin and diazoxide can be used as optional hair growth regulating agents in the compositions herein.

One suitable class of optional activity enhancer for use herein are anti-androgens. Examples of suitable anti-androgens may include, but are not limited 5-α-reductase inhibitors such as finesteride and those described in U.S. Pat. No. 5,516,779, issued May 14, 1996 (herein incorporated by reference) and in Nnane et al, *Cancer Research* 58, "Effects of Some Novel Inhibitors of C17,20-Lyase and 5α-Reductase in Vitro and in Vivo and Their Potential Role in the Treatment of Prostate Cancer., as well as cyproterone acetate, azelaic acid and its derivatives and those compounds described in U.S. Pat. No. 5,480,913, issued Jan. 2, 1996, flutamide, and those described in U.S. Pat. No. 5,411,981, issued May 2, 1995, U.S. Pat. No. 5,565,467, issued Oct. 15, 1996 and U.S. Pat. No. 4,910,226, issued Mar. 20, 1990, all of which are herein incorporated by reference.

Another suitable class of optional hair growth regulating agents are immunosuppressants such as 1) cyclosporin and cyclosporin analogs including those described in U.S. Provisional Patent Application No. 60/122,925, Fulmer et al., "Method of Treating Hair Loss Using Non-Immunosuppressive Compounds", filed Mar. 5, 1999, herein incorporated by reference, and 2) FK506 analogs such as those described in U.S. Provisional Patent Application No. 60/102,449, McIver et al., "Heterocyclic 2-Substituted Ketoamides", filed Sep. 30, 1998, U.S. Provisional Patent Application No. 60/102,448, McIver et al., "2-Substituted Ketoamides", filed Sep. 30, 1998, U.S. Provisional Patent Application No. 60/102,539, McIver et al., "2-Substituted Heterocyclic Sulfonamides", filed Sep. 30, 1998, U.S. Provisional Patent Application No. 60/102,458, Tiesman et al., "Method of Treating Hair Loss Using Ketoamides", filed Sep. 30, 1998, and U.S. Provisional Patent Application No. 60/102,437, McIver et al., "Method of Treating Hair Loss Using Sulfonamides", filed Sep. 30, 1998, all of which are herein incorporated by reference.

Another suitable class of optional hair growth regulating agents are antimicrobials such as selenium sulfide, ketoconazole, triclocarbon, triclosan, zinc pyrithione, itraconazole, asiatic acid, hinokitiol, mipirocin and those described in EPA 0,680,745 (herein incorporated by reference), clinacycin hydrochloride, benzoyl peroxide, benzyl peroxide and minocyclin.

Anti-inflammatories can also be incorporated into the compositions herein as an optional activity enhancer. Examples of suitable anti-inflammatories may include glucocorticoids such as hydrocortisone, mometasone furoate and prednisolone, nonsteroidal anti-inflammatories including cyclooxygenase or lipoxygenase inhibitors such as those described in U.S. Pat. No. 5,756,092, and benzydamine, salicylic acid, and those compounds described in EPA 0,770,399, published May 2, 1997, WO 94/06434, published Mar. 31, 1994 and FR 2,268,523, published Nov. 21, 1975, all of which are herein incorporated by reference.

Another suitable class of optional hair growth regulating agents are thyroid hormones and derivatives and analogs thereof. Examples of suitable thyroid hormones for use herein may include triiodothyrionine. Examples of thyroid hormone analogs which may be suitable for use herein include those described in U.S. Provisional Patent Application No. 60/136,996, Zhang et al., "Method of Treating Hair Loss", filed Jun. 1, 1999, U.S. Provisional Patent Application No. 60/137,024, Zhang et al., "Method of Treating Hair Loss Using Biphenyl Compounds", filed Jun. 1, 1999, U.S. Provisional Patent Application No. 60/137,022, Zhang et al., "Method of Treating Hair Loss Using Carboxyl Derivatives", filed Jun. 1, 1999, U.S. Provisional Patent Application No. 20 60/137,023, Zhang et al., "Method of Treating Hair Loss Using Sulfonyl Thyromimetic Compounds", filed Jun. 1, 1999, U.S. Provisional Patent Application No. 60/137,052, Youngquist et al., "Biaryl Compounds", filed Jun. 1, 1999, U.S. Provisional Patent Application No. 60/137,063, Youngquist et al., "Sulfur-Bridged Compounds", filed Jun. 1, 1999, and U.S. Provisional Patent Application No. 60/136,958, Youngquist et al., "Substituted Biaryl Ether Compounds", filed Jun. 1, 1999.

Prostaglandin agonists or antagonists can also be used as optional hair growth regulating agents in the compositions herein. Examples of suitable prostaglandins agonists or antagonists include latanoprost and those described in WO 98/33497, Johnstone, published Aug. 6, 1998, WO 95/11003, Stjernschantz, published Apr. 27, 1995, JP 97-100091, and Ueno, JP 96-134242, Nakamura.

Another class of optional hair growth regulating agents for use herein are retinoids. Suitable retinoids may include isotretinoin, acitretin, tazarotene, Non-limiting examples of penetration enhancers which may be used as optional hair growth regulating agents herein include, for example, 2-methyl propan-2-ol, propan-2-ol, ethyl-2-hydroxypropanoate, hexan-2,5-diol, POE(2) ethyl ether, di(2-hydroxypropyl) ether, pentan-2,4-diol, acetone, POE(2) methyl ether, 2-hydroxypropionic acid, 2-hydroxyoctanoic acid, propan-1-ol, 1,4-dioxane, tetrahydrofuran, butan-1,4-diol, propylene glycol dipelargonate, polyoxypropylene 15 stearyl ether, octyl alcohol, POE ester of oleyl alcohol, oleyl alcohol, lauryl alcohol, dioctyl adipate, dicapryl adipate, di-isopropyl adipate, di-isopropyl sebacate, dibutyl sebacate, diethyl sebacate, dimethyl sebacate, dioctyl sebacate, dibutyl suberate, dioctyl azelate, dibenzyl sebacate, dibutyl phthalate, dibutyl azelate, ethyl myristate, dimethyl azelate, butyl myristate, dibutyl succinate, didecyl phthalate, decyl oleate, ethyl caproate, ethyl salicylate, iso-propyl palmitate, ethyl laurate, 2-ethyl-hexyl pelargonate, iso-propyl isostearate, butyl laurate, benzyl benzoate, butyl benzoate, hexyl laurate, ethyl caprate, ethyl caprylate, butyl stearate, benzyl salicylate, 2-hydroxypropanoic acid, 2-hyroxyoctanoic acid, methylsulfoxide, N,N-dimethyl acetamide, N,N-dimethyl formamide, 2-pyrrolidone, 1-methyl-2-pyrrolidone, 5-methyl-2-pyrrolidone, 1,5-dimethyl-2-pyrrolidone, 1-ethyl-2-pyrrolidone, phosphine oxides, sugar esters, tetrahydrofurfural alcohol, urea, diethyl-m-toluamide, 1-dodecylazacyloheptan-2-one and those described in U.S. Pat. No. 5,015,470, issued May 14, 1991 and U.S. Pat. No. 5,496,827, issued Jul. 15, 1994 (both of which are herein incorporated in its entirety by reference).

Other classes of optional hair growth regulating agents for use herein include flavinoids, ascomycin derivatives and analogs, histamine antagonists such as diphenhydramine hydrochloride, other triterpenes such as oleanolic acid and ursolic acid and those described in U.S. Pat. No. 5,529,769, JP 10017431, WO 95/35103, U.S. Pat. No. 5,468,888, JP 09067253, WO 92/09262, JP 62093215, U.S. Pat. No. 5,631,282, U.S. Pat. No. 5,679,705, JP 08193094, saponins such as those described in EP 0,558,509 to Bonte et al, published Sep. 8, 1993 and WO 97/01346 to Bonte et al, published Jan. 16, 1997 (both of which are herein incorporated by reference in their entirety), proeoglycanase or glycosaminoglycanase inhibitors such as those described in U.S. Pat. No. 5,015,470, issued May 14, 1991, U.S. Pat. No. 5,300,284, issued Apr. 5, 1994 and U.S. Pat. No. 5,185,325, issued Feb. 9, 1993 (all of which are herein incorporated in their entirety by reference) estrogen agonists and antagonists, pseudoterins, cytokine and growth factor promotors, analogs or inhibitors such as interleukin1 inhibitors, interleukin-6 inhibitors, interleukin-10 promotors, and tumor necrosis factor inhibitors, vitamins such as vitamin D analogs and parathyroid hormone antagonists, Vitamin B12 analogs and panthenol, interfuron agonists and antagonists, hydroxyacids such as those described in U.S. Pat. No. 5,550,158, benzophenones and hydantoin anticonvulsants such as phenytoin.

Other hair growth agents are described in detail in, for example, JP 09-157,139 to Tsuji et al, published Jun. 17, 1997; EP 0277455 Al to Mirabeau, published Aug. 10, 1988; WO 97/05887 to Cabo Soler et al, published Feb. 20, 1997; WO 92/16186 to Bonte et al, published Mar. 13, 1992; JP 62-93215 to Okazaki et al, published Apr. 28, 1987; U.S. Pat. No. 4,987,150 to Kurono et al, issued Jan. 22, 1991; JP 290811 to Ohba et al, published Oct. 15, 1992; JP 05-286, 835 to Tanaka et al, published Nov. 2, 1993, FR 2,723,313 to Greff, published Aug. 2, 1994, U.S. Pat. No. 5,015,470 to Gibson, issued May 14, 1991, U.S. Pat. No. 5,559,092, issued Sep. 24, 1996, U.S. Pat. No. 5,536,751, issued Jul. 16, 1996, U.S. Pat. No. 5,714,515, issued Feb. 3, 1998, EPA 0,319,991, published Jun. 14, 1989, EPA 0,357,630, published Oct. 6, 1988, EPA 0,573,253, published Dec. 8, 1993, JP 61-260010, published Nov. 18, 1986, U.S. Pat. No. 5,772,990, issued Jun. 30, 1998, U.S. Pat. No. 5,053, 410, issued Oct. 1, 1991, and U.S. Pat. No. 4,761,401, issued Aug. 2, 1988, all of which are herein incorporated by reference.

Some preferred hair growth regulating agents for use herein are zinc salts of carboxylic acids, saponins, triterpenes, oleanolic acid, ursolic acid, betulinic acid, betulonic acid, crataegolic acid, celastrol, asiatic acid, inhibitors of 5-α-reductase, progesterone, 1,4-methyl-4-azasteroids, 17-β-N,N-diethylcarbamoyl-4-methyl-4-aza-5-α-androstan-3-one, androgen receptor antagonists, cyproterone acetate, minoxidil, azelaic acid and derivatives thereof, cyclosporin, triiodothyronine, diazoxide, potassium channel openers, cromakalin, phenytoin, ketoconazole, finesteride, dutasteride, coal tar, zinc gluconate, glucocortisoids, macrolides, aminexil, and mixtures thereof.

D. Other Optional Ingredients

The anti-dandruff and conditioning shampoo compositions of the present invention may, in some embodiments, further comprise additional optional components known or otherwise effective for use in hair care or personal care products. The concentration of such optional ingredients generally ranges from zero to about 25%, more typically from about 0.05% to about 25%, even more typically from about 0.1% to about 15%, by weight of the composition. Such optional components should also be physically and chemically compatible with the essential components described herein, and should not otherwise unduly impair product stability, aesthetics or performance.

Non limiting examples of optional components for use in the shampoo composition include anti-static agents, foam boosters, soluble anti-dandruff agents, viscosity adjusting agents and thickeners, pH adjusting agents (e.g. sodium citrate, citric acid, succinic acid, phosphoric acid, sodium hydroxide, and sodium carbonate), preservatives (e.g. DMDM hydantoin), anti-microbial agents (e.g. triclosan or triclocarbon), dyes, organic solvents or diluents, pearlescent aids, perfumes, fatty alcohols, proteins, skin active agents, sunscreens, vitamins, and pediculocides.

Optional anti-static agents such as water-insoluble cationic surfactants may be used, typically in concentrations ranging from about 0.1% to about 5%, by weight of the composition. Such anti-static agents should not unduly interfere with the in-use performance and end-benefits of the shampoo composition; particularly, the anti-static agent should not interfere with the anionic surfactant. A specific non-limiting example of a suitable anti-static agents is tricetyl methyl ammonium chloride.

Optional foam boosters for use in the shampoo compositions described herein include fatty ester (e.g. $C_8$–$C_{22}$) mono- and di ($C_1$–$C_5$, especially $C_1$–$C_3$) alkanol amides. Specific non-limiting examples of such foam boosters include coconut monoethanolamide, coconut diethanolamide, and mixtures thereof.

Optional anti-dandruff agents may be used in addition to the particulate anti-dandruff actives of the present invention, typically in concentrations ranging from about 0.1% to about 4%, by weight of the composition, preferably from about 0.2% to about 2%. Such optional anti-dandruff agents include soluble anti-dandruff agents, specific non-limiting examples of which include: piroctone olamine, ketoconazol, and mixtures thereof.

Optional viscosity modifiers and thickeners may used, typically in amounts effective for the anti-dandruff and conditioning shampoo compositions of the present invention to generally have an overall viscosity from about 1,000 csk to about 20,000 csk, preferably from about 3,000 csk to about 10,000 csk. Specific non-limiting examples of such viscosity modifiers and thickeners include: sodium chloride, sodium sulfate, and mixtures thereof.

III. Methods of Manufacture

The anti-dandruff and conditioning shampoo compositions of the present invention may be prepared by any known or otherwise effective technique, suitable for providing a shampoo composition provided that the resulting composition provides the excellent hair feel benefits described herein. Methods for preparing the anti-dandruff and conditioning shampoos of the present invention include conventional formulation and mixing techniques. A method such as that described in U.S. Pat. No. 5,837,661, which description is incorporated herein by reference, could be employed, wherein the anti-dandruff particulate of the present invention would typically be added in the same step as the silicone premix is added in the '661 description.

IV. Methods of Use

The anti-dandruff and conditioning shampoo compositions of the present invention are used in a conventional manner for cleansing and conditioning the hair or skin. They are particularly used in a conventional manner for treating the condition commonly known as dandruff. An effective amount of the composition for cleansing and conditioning the hair or skin is applied to hair, or other region of the body, that has preferably been wetted, generally with water, and then the composition is rinsed off. Effective amounts typically range from about 1 g to about 50 g, preferably from about 1 g to about 20 g. Application to the hair typically includes working the composition through the hair such that most or all of the hair is contacted with the composition.

This method for providing anti-dandruff efficacy and conditioning hair comprises the steps of: (a) wetting the hair with water, (b) applying an effective amount of the shampoo composition to the hair, and (c) rinsing the shampoo composition from the hair using water. These steps may be repeated as many times as desired to achieve the cleansing, conditioning, and anti-dandruff benefits sought.

It is also contemplated that when the anti-dandruff particulate employed is zinc pyrithione, and/or if other optional hair growth regulating agents are employed, the shampoo compositions of the present invention, may, provide for the regulation of growth of the hair. The method of regularly using such shampoo compositions comprises steps a, b, and c (above).

EXAMPLES

The following are non-limiting examples of the anti-dandruff and conditioning shampoo compositions of the present invention. The examples are given solely for the purpose of illustration and are not to be construed as limitations of the present invention, as many variations thereof are possible without departing from the spirit and scope of the invention, which would be recognized by one of ordinary skill in the art. In the examples, all concentrations are listed as weight percent, unless otherwise specified. As used herein, "minors" refers to those optional components such as preservatives, viscosity modifiers, pH modifiers, fragrances, foam boosters, and the like. As is apparent to one of ordinary skill in the art, the selection of these minors will vary depending on the physical and chemical characteristics of the particular ingredients selected to make the present invention as described herein.

A suitable method for preparing the anti-dandruff and conditioning shampoo compositions described in Examples I–XV (below) follows: About one-third to all of the ammonium laureth sulfate (added as 25 wt % solution) is added to a jacketed mix tank and heated to about 60° C. to about 80° C. with slow agitation to form a surfactant solution. Cocamide MEA and fatty alcohols, (where applicable), are added to the tank and allowed to disperse. Salts (e.g. sodium chloride) and pH modifiers (e.g. citric acid, sodium citrate) are added to the tank and allowed to disperse. Ethylene glycol distearate ("EGDS") is added to the mixing vessel and allowed to melt. After the EGDS is melted and dispersed, preservative is added to the surfactant solution. The resulting mixture is cooled to about 25° C. to about 40° C. and collected in a finishing tank. As a result of this cooling step, the EGDS crystallizes to form a crystalline network in the product. The remainder of the ammonium laureth sulfate and other components, including the silicone and anti-dandruff particulate, are added to the finishing tank with agitation to ensure a homogeneous mixture. Cationic polymer is dispersed in water as an about 0.1% to about 10% aqueous solution and then added to the final mix. Once all components have been added, additional viscosity and pH modifiers may be added, as needed, to the mixture to adjust product viscosity and pH to the extent desired.

| | Example Number | | | | |
|---|---|---|---|---|---|
| | I | II | III | IV | V |
| Ammonium Laureth Sulfate | 12 | 12 | 11 | 10 | 12 |
| Ammonium Lauryl Sulfate | 8 | 8 | 7 | 6 | 6 |
| Guar Hydroxypropyltrimonium Chloride[1] | 0.4 | 0.4 | 0.25 | 0.6 | 0.6 |
| PEG 23M[2] | — | — | — | — | 0.1 |
| PEG 90M[3] | 0.1 | 0.05 | 0.025 | 0.01 | — |
| Zinc Pyrithione[4] | 1 | 1 | 1 | 1 | 1 |
| 1-decene homopolymer[5] | 0.2 | 0.3 | 0.3 | 0.5 | 0.4 |
| Trimethylpropane Capyl Caprylate[6] | 0.2 | 0.1 | 0.1 | 0.0 | 0.1 |
| Dimethicone[7] | 1.0 | 2.0 | 0.8 | 0.5 | 1.25 |
| Ethylene Glycol Distearate | 1.0 | 2.0 | 1.5 | 2.0 | 1.5 |
| Cocamide MEA | 0.6 | 0.8 | 0.6 | 0.8 | 1.0 |
| Cetyl Alcohol | 0.9 | 0.9 | 0.9 | 0.9 | 1.0 |
| Water and minors | quantity sufficient | | | | |

[1]Guar having a molecular weight of about 200,000, and having a charge density of about 0.71 meq/g, available from Aqualon.
[2]Polyox WSR N-12k, available from Union Carbide.
[3]Polyox WSR 301, available from Union Carbide.
[4]ZPT having an average particle size of about 2.5 μm, available from Arch/Olin.
[5]Puresyn 6, available from Mobil.
[6]Mobil P43, available from Mobil.
[7]Visasil 330,000 csk, available from General Electric Silicones.

| | Example Number | | | | |
|---|---|---|---|---|---|
| | VI | VII | VIII | IX | X |
| Ammonium Laureth Sulfate | 12 | 12 | 10 | 10 | 12 |
| Ammonium Lauryl Sulfate | 8 | 6 | 6 | 5 | 6 |
| Polyquaternium-10[1] | — | — | 0.25 | 0.25 | 0.1 |
| Guar Hydroxypropyltrimonium Chloride[2] | — | 0.25 | — | — | — |
| Guar Hydroxypropyltrimonium Chloride[3] | 0.5 | — | 0.25 | 0.35 | 0.4 |
| PEG 7M[4] | 0.1 | — | 0.1 | 0.1 | 0.2 |
| PEG 90M[5] | — | 0.1 | — | — | — |
| Zinc Pyrithione[6] | 1 | 1 | 1 | 1 | 1 |
| 1-decene homopolymer[7] | 0.2 | 0.4 | 0.4 | 0.5 | 0.5 |
| Trimethylpropane Capyl Caprylate[8] | 0.1 | — | 0.1 | 0.2 | — |
| Dimethicone[9] | 0.55 | 1.15 | 1.35 | 3.25 | 3.35 |
| Ethylene Glycol Distearate | 1.5 | 1.0 | 1.5 | 2.0 | 2.0 |

-continued

| | | | | | |
|---|---|---|---|---|---|
| Cocamide MEA | 0.6 | 1.1 | 0.8 | 1.1 | 1.3 |
| Cetyl Alcohol | 0.9 | 0.6 | 0.9 | 1.0 | 1.0 |
| Water and minors | | | quantity sufficient | | |

[1] UCARE Polymer LR400, available from Amerchol.
[2] Jaguar C17, available from Rhodia.
[3] Guar having a molecular weight of about 200,000, and having a charge density of about 0.71 meq/g, available from Aqualon.
[4] Polyox WSR N-750, available from Union Carbide
[5] Polyox WSR 301, available from Union Carbide.
[6] ZPT having an average particle size of about 2.5 µm, available from Arch/Olin.
[7] Puresyn 6, available from Mobil.
[8] Mobil P43, available from Mobil.
[9] Visasil 330,000 csk, available from General Electric Silicones.

| | Example Number | | | | |
|---|---|---|---|---|---|
| | XI | XII | XIII | XIV | XV |
| Ammonium Laureth Sulfate | 10 | 11 | 12 | 13 | 12 |
| Ammonium Lauryl Sulfate | 6 | 7 | 7 | 5 | 5 |
| Polyquaternium-10[1] | 0.15 | — | — | — | — |
| Guar Hydroxypropyltrimonium Chloride[2] | — | — | 0.1 | — | — |
| Guar Hydroxypropyltrimonium Chloride[3] | — | 0.4 | — | 0.1 | — |
| Guar Hydroxypropyltrimonium Chloride[4] | — | — | — | — | 0.5 |
| Guar Hydroxypropyltrimonium Chloride[5] | 0.25 | — | — | — | — |
| PEG 90M[6] | 0.025 | 0.1 | 0.15 | 0.15 | 0.2 |
| Zinc Pyrithione[7] | 1 | 1 | 1 | 1 | 1 |
| 1-decene homopolymer[8] | 0.6 | 0.2 | 0.4 | — | 0.1 |
| Trimethylpropane Capyl Caprylate[9] | — | — | 0.3 | 0.2 | 0.1 |
| Dimethicone[10] | 1.35 | 1.45 | 0.75 | 1.1 | 0.85 |
| Ethylene Glycol Distearate | 1.0 | 1.2 | 1.5 | 2.0 | 2.0 |
| Cocamide MEA | 0.6 | 1.0 | 0.6 | 0.6 | 1.1 |
| Cetyl Alcohol | 0.9 | 1.0 | 0.6 | 0.6 | 1.1 |
| Water and minors | | | quantity sufficient | | |

[1] UCARE Polymer LR400, available from Amerchol.
[2] Jaguar C17, available from Rhodia.
[3] Jaguar C14S, available from Rhodia.
[4] Guar having a molecular weight of about 900,000, and having a charge density of about 0.71 meq/g, available from Aqualon.
[5] Guar having a molecular weight of about 200,000, and having a charge density of about 0.71 meq/g, available from Aqualon.
[6] Polyox WSR 301, available from Union Carbide.
[7] ZPT having an average particle size of about 2.5 µm, available from Arch/Olin.
[8] Puresyn 6, available from Mobil.
[9] Mobil P43, available from Mobil.
[10] Visasil 330,000 csk, available from General Electric Silicones.

What is claimed:
1. A shampoo composition comprising:
   a) from about 5% to about 50%, by weight of the composition, of an anionic surfactant;
   b) from about 0.01% to about 10%, by weight of the composition, of a non-volatile conditioning agent;
   c) from about 0.1% to about 4%, by weight of the composition, of an anti-dandruff particulate;
   d) from about 0.02% to about 5%, by weight of the composition, of at least one cationic polymer;
   e) from 0.005% to about 1.5%, by weight of the composition, of a polyalkylene glycol corresponding to the formula:

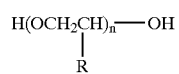

i) wherein R is selected from the group consisting of hydrogen, methyl and mixtures thereof,
   ii) wherein n is an integer having an average value from about 1,500 to about 120,000; and
f) water.

2. A shampoo composition according to claim 1, wherein said at least one cationic polymer component is selected from the group consisting of guar derivatives, cellulose derivatives, and mixtures thereof.

3. A shampoo composition according to claim 2, wherein at least one of said guar derivatives is guar hydroxypropyltrimonium chloride.

4. A shampoo composition according to claim 2, wherein at least one of said cellulose derivatives is polyquaternium-10.

5. A shampoo composition according to claim 1, comprising from about 0.1% to about 1%, by weight of the composition, of said at least one cationic polymer.

6. A shampoo composition according to claim 2, wherein said guar derivatives have a molecular weight from about 50,000 to about 700,000.

7. A shampoo composition according to claim 2, wherein said guar derivatives have a charge density from about 0.05 meq/g to about 0.9 meq/g.

8. A shampoo composition according to claim 2, wherein said cellulose derivatives have a molecular weight from about 200,000 to about 1,500,000.

9. A shampoo composition according to claim 8, wherein said cellulose derivatives have a molecular weight from about 350,000 to about 500,000.

10. A shampoo composition according to claim 2, wherein said cellulose derivatives have a charge density from about 0.2 meq/g to about 0.6 meq/g.

11. A shampoo composition according to claim 1, wherein said non-volatile conditioning agent comprises silicone.

12. A shampoo composition according to claim 1, wherein said polyalkylene glycol has an average value of n from about 1,500 to about 50,000.

13. A shampoo composition according to claim 1, wherein said anti-dandruff particulate is a zinc salt of 1-hydroxy-2-pyridinethione.

14. A shampoo composition according to claim 13, wherein the said zinc salt of 1-hydroxy-2-pyridinethione is in platelet particle form.

15. A shampoo composition according to claim 1, wherein said anti-dandruff particulate has a average particle size of about 2.5 µm.

16. A shampoo composition according to claim 1, comprising from about 0.3% to about 2%, by weight of the composition, of said anti-dandruff particulate.

17. A shampoo composition according to claim 1, wherein said composition further comprises from about 0.1% to about 10%, by weight of the composition, of a suspending agent.

18. A shampoo composition according to claim 17, wherein said suspending agent is ethylene glycol distearate.

19. A shampoo composition comprising:
   a) from about 10% to about 25%, by weight of the composition, of an anionic surfactant;
   b) from about 0.01% to about 10%, by weight of the composition, of an insoluble, non-volatile silicone conditioning agent;
   c) from about 0.3% to about 2%, by weight of the composition, of a zinc salt of 1-hydroxy-2-pyridinethione;
   d) from about 0.1% to about 2%, by weight of the composition, of at least one cationic polymer selected from the group consisting of guar derivatives, cellulose derivatives, and mixtures thereof;
   e) from 0.025% to about 1.5%, by weight of the composition, of a polyalkylene glycol corresponding to the formula:

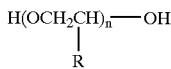

i) wherein R is selected from the group consisting of hydrogen, methyl and mixtures thereof, ii) wherein n is an integer having an average value from about 3,500 to about 15,000; and f) water.

20. A method for providing anti-dandruff efficacy and conditioning hair comprising:

a) wetting said hair with water;

b) applying to said hair an effective amount of a shampoo composition according to claim 1; and c) rinsing said shampoo composition from said hair using water.

21. A shampoo composition according to claim 13, further comprising from about 0.001% to about 15% of a hair growth regulating agent selected from the group consisting of zinc salts of carboxylic acids, saponins, triterpenes, oleanolic acid, ursolic acid, betulinic acid, betulonic acid, crataegolic acid, celastrol, asiatic acid, inhibitors of 5-α-reductase, progesterone, 1,4-methyl-4-azasteroids, 17-β-N,N-diethylcarbamoyl-4-methyl-4-aza-5-α-androstan-3-one, androgen receptor antagonists, cyproterone acetate, minoxidil, azelaic acid and derivatives thereof, cyclosporin, triiodothyronine, diazoxide, potassium channel openers, cromakalin, phenytoin, ketoconazole, finesteride, dutasteride, coal tar, zinc gluconate, glucocortisoids, macrolides, aminexil, and mixtures thereof.

22. A method for regulating the growth of the hair comprising:

a) wetting said hair with water;

b) applying to said hair an effective amount, of a shampoo composition according to claim 15;

c) rinsing said shampoo composition from said hair using water.

23. A method for regulating the growth of the hair comprising:

a) wetting said hair with water;

b) applying to said hair an effective amount, of a shampoo composition according to claim 23;

c) rinsing said shampoo composition from said hair using water.

24. A shampoo composition according to claim 16, wherein said polyalkylene glycol has an average value of n from about 3,500 to about 15,000.

25. A shampoo composition according to claim 18, comprising from about 0.025% to about 1.5%, by weight of the composition, of said polyalkylene glycol.

* * * * *

(12) INTER PARTES REVIEW CERTIFICATE (100th)
United States Patent
Dunlop et al.

(10) Number: US 6,451,300 K1
(45) Certificate Issued: Sep. 15, 2015

(54) ANTI-DANDRUFF AND CONDITIONING SHAMPOOS CONTAINING POLYALKYLENE GLYCOLS AND CATIONIC POLYMERS

(75) Inventors: David Scott Dunlop; Susan Marie Guskey; Vicente Eduardo Leyba; Douglas Allan Royce

(73) Assignee: THE PROCTER & GAMBLE COMPANY

Trial Number:

IPR2013-00509 filed Aug. 14, 2013

Petitioner: Conopco, Inc. dba Unilever

Patent Owner: The Procter & Gamble Company

Inter Partes Review Certificate for:

Patent No.: 6,451,300
Issued: Sep. 17, 2002
Appl. No.: 09/558,447
Filed: Apr. 25, 2000

The results of IPR2013-00509 are reflected in this inter partes review certificate under 35 U.S.C. 318(b).

INTER PARTES REVIEW CERTIFICATE
U.S. Patent 6,451,300 K1
Trial No. IPR2013-00509
Certificate Issued Sep. 15, 2015

AS A RESULT OF THE INTER PARTES REVIEW PROCEEDING, IT HAS BEEN DETERMINED THAT:

Claims 1-5, 11-13, 16-20, 24 and 25 are cancelled.

\* \* \* \* \*